(12) United States Patent
Goldberg

(10) Patent No.: US 10,973,646 B2
(45) Date of Patent: Apr. 13, 2021

(54) STABILIZED DRILL GUIDE

(71) Applicant: Catalyst OrthoScience Inc., Naples, FL (US)

(72) Inventor: Steven S. Goldberg, Naples, FL (US)

(73) Assignee: Catalyst OrthoScience Inc., Naples, FL (US)

( * ) Notice: Subject to any disclaimer, the term of this patent is extended or adjusted under 35 U.S.C. 154(b) by 0 days.

(21) Appl. No.: 15/660,942

(22) Filed: Jul. 26, 2017

(65) Prior Publication Data

US 2017/0348112 A1 Dec. 7, 2017

Related U.S. Application Data

(63) Continuation-in-part of application No. 14/042,258, filed on Sep. 30, 2013, now Pat. No. 9,775,716, and
(Continued)

(51) Int. Cl.
*A61B 17/04* (2006.01)
*A61B 17/15* (2006.01)
(Continued)

(52) U.S. Cl.
CPC ........ *A61F 2/4081* (2013.01); *A61B 17/1604* (2013.01); *A61B 17/1684* (2013.01); *A61B 17/1778* (2016.11); *A61F 2/30771* (2013.01); *A61F 2/4657* (2013.01); *A61B 17/1659* (2013.01); *A61F 2002/30156* (2013.01); *A61F 2002/30878* (2013.01); *A61F 2002/30881* (2013.01); *A61F 2002/30884* (2013.01);
(Continued)

(58) Field of Classification Search
CPC ....... A61B 17/17; A61B 17/15; A61B 17/157; A61B 17/846; A61B 17/16; A61B 17/32; A61B 5/4504; A61B 5/4528; A61B 17/1615; A61B 17/1659
See application file for complete search history.

(56) References Cited

U.S. PATENT DOCUMENTS 4,106,130 A 8/1978 Scales
4,206,517 A 6/1980 Pappas
(Continued)

FOREIGN PATENT DOCUMENTS

AU 2013209336 2/2014
AU 2014249514 10/2015
(Continued)

*Primary Examiner* — Ann Schillinger
(74) *Attorney, Agent, or Firm* — Maywood IP Law; David Meibos

(57) ABSTRACT

A drill guide includes a working portion and a shaft, with a joint formed between the working portion and the shaft so that the shaft is movable relative to the working portion about the joint. The working portion includes at least one drill guide hole which receives a drill for making a hole in a bone. The joint isolates the working portion from unintentional movements of the shaft so that the working portion remains stable against a bone surface. The joint also enables the shaft to be used as a retractor or pry bar against surrounding anatomical structures if desired. The drill guide may be included in a system with an implant component and/or other surgical instruments.

16 Claims, 29 Drawing Sheets

Related U.S. Application Data a continuation-in-part of application No. 15/587,895, filed on May 5, 2017, now abandoned, and a continuation-in-part of application No. 14/592,837, filed on Jan. 8, 2015, now Pat. No. 9,814,471, and a continuation-in-part of application No. 15/228,443, filed on Aug. 4, 2016, now Pat. No. 9,814,588, and a continuation-in-part of application No. 15/653,305, filed on Jul. 18, 2017, now abandoned, said application No. 15/587,895 is a continuation of application No. 14/042,258, filed on Sep. 30, 2013, now Pat. No. 9,775,716, said application No. 14/592,837 is a continuation-in-part of application No. 14/042,258, filed on Sep. 30, 2013, now Pat. No. 9,775,716, said application No. 15/653,305 is a continuation-in-part of application No. 15/228,443, filed on Aug. 4, 2016, now Pat. No. 9,814,588.

(60) Provisional application No. 62/367,533, filed on Jul. 27, 2016, provisional application No. 61/776,398, filed on Mar. 11, 2013, provisional application No. 61/925,893, filed on Jan. 10, 2014, provisional application No. 62/203,255, filed on Aug. 10, 2015, provisional application No. 62/363,607, filed on Jul. 18, 2016.

(51) Int. Cl.
| | |
|---|---|
| *A61F 2/40* | (2006.01) |
| *A61B 17/17* | (2006.01) |
| *A61F 2/30* | (2006.01) |
| *A61B 17/16* | (2006.01) |
| *A61F 2/46* | (2006.01) |

(52) U.S. Cl.
CPC ........... *A61F 2002/30892* (2013.01); *A61F 2002/30902* (2013.01); *A61F 2002/30904* (2013.01); *A61F 2002/4658* (2013.01)

(56) References Cited

U.S. PATENT DOCUMENTS

| | | | |
|---|---|---|---|
| 4,550,450 A | 11/1985 | Kinnett | |
| 4,795,468 A | 1/1989 | Hodorek | |
| 4,865,605 A | 9/1989 | Dines | |
| 4,936,853 A | 6/1990 | Fabian | |
| 4,964,865 A | 10/1990 | Burkhead | |
| 4,986,833 A | 1/1991 | Worland | |
| 5,030,219 A * | 7/1991 | Matsen, III | A61B 17/1624 606/53 |
| 5,032,132 A | 7/1991 | Matsen, III | |
| 5,383,936 A | 1/1995 | Kubein-Meesenburg | |
| 5,489,309 A | 2/1996 | Lackey | |
| 5,489,310 A | 2/1996 | Mikhail | |
| 5,593,448 A | 1/1997 | Dong | |
| 5,702,447 A | 12/1997 | Walch | |
| 5,723,018 A | 3/1998 | Cyprien | |
| 5,769,856 A | 6/1998 | Dong | |
| 5,800,551 A * | 9/1998 | Williamson | A61B 17/1659 623/19.11 |
| 5,814,049 A | 9/1998 | Pratt | |
| 5,851,207 A | 12/1998 | Cesarone | |
| 5,919,195 A | 7/1999 | Wilson | |
| 5,928,285 A | 7/1999 | Bigliani | |
| 5,944,758 A | 8/1999 | Mansat | |
| 5,976,144 A | 11/1999 | Fishbein | |
| 6,129,732 A | 10/2000 | Lechot | |
| 6,245,074 B1 | 6/2001 | Allard | |
| 6,364,910 B1 | 4/2002 | Shultz | |
| 6,379,386 B1 | 4/2002 | Resch | |
| 6,406,495 B1 | 6/2002 | Schoch | |
| 6,475,221 B1 | 11/2002 | White | |
| 6,673,115 B2 | 1/2004 | Resch | |
| 6,679,916 B1 | 1/2004 | Frankle | |
| 6,699,289 B2 | 3/2004 | Iannotti | |
| 6,783,549 B1 | 8/2004 | Stone | |
| 6,875,234 B2 | 4/2005 | Lipman | |
| 6,911,047 B2 | 6/2005 | Rockwood, Jr. | |
| 7,008,430 B2 | 3/2006 | Dong | |
| 7,048,740 B2 | 5/2006 | White | |
| 7,160,328 B2 | 1/2007 | Rockwood, Jr. | |
| 7,204,854 B2 | 4/2007 | Guederian | |
| 7,217,272 B2 | 5/2007 | Salyer | |
| 7,294,149 B2 | 11/2007 | Hozack | |
| 7,329,284 B2 | 2/2008 | Maroney | |
| 7,588,572 B2 | 9/2009 | White | |
| 7,621,962 B2 | 11/2009 | Lakin | |
| 7,670,382 B2 | 3/2010 | Parrott | |
| 7,780,669 B2 | 8/2010 | Lechot | |
| 7,815,685 B2 | 10/2010 | Farrar | |
| 7,867,234 B2 | 1/2011 | Collazo | |
| 7,892,287 B2 | 2/2011 | Deffenbaugh | |
| 8,007,538 B2 | 8/2011 | Gunther | |
| 8,038,719 B2 | 10/2011 | Gunther | |
| 8,048,161 B2 | 11/2011 | Guederian | |
| 8,080,063 B2 | 12/2011 | Ferrand | |
| 8,157,866 B2 | 4/2012 | Winslow | |
| 8,308,809 B2 | 11/2012 | Bishop | |
| 8,425,614 B2 | 4/2013 | Winslow | |
| 8,444,646 B2 | 5/2013 | Long | |
| 8,465,548 B2 | 6/2013 | Long | |
| 8,475,460 B1 | 7/2013 | Roger | |
| 8,480,674 B1 | 7/2013 | Roger | |
| 8,540,778 B2 | 9/2013 | Rhodes | |
| 8,556,980 B2 | 10/2013 | Deffenbaugh | |
| 8,591,592 B2 | 11/2013 | Dreyfuss | |
| 8,673,015 B2 | 3/2014 | Maroney | |
| 8,764,836 B2 | 7/2014 | De Wilde | |
| 8,778,028 B2 | 7/2014 | Gunther | |
| 8,870,962 B2 | 10/2014 | Roche | |
| 8,876,907 B2 | 11/2014 | Baptista | |
| 8,974,537 B2 | 3/2015 | Dreyfuss | |
| 8,986,309 B1 * | 3/2015 | Murphy | A61B 17/1746 606/87 |
| D730,522 S | 5/2015 | Goldberg | |
| 9,119,643 B2 | 9/2015 | Winslow | |
| 9,180,016 B2 | 11/2015 | Maroney | |
| 9,233,003 B2 | 1/2016 | Roche | |
| 9,237,894 B2 | 1/2016 | Hernandez | |
| 9,283,076 B2 | 3/2016 | Sikora | |
| 9,289,306 B2 | 3/2016 | Goldberg | |
| 9,345,578 B2 | 5/2016 | Collazo | |
| 9,351,844 B2 | 5/2016 | Walch | |
| D759,819 S | 6/2016 | Goldberg | |
| 9,370,428 B2 | 6/2016 | Winslow | |
| 9,433,507 B2 | 9/2016 | Reubelt | |
| 9,474,619 B2 | 10/2016 | Reubelt | |
| 9,610,166 B2 | 4/2017 | Gunther | |
| D810,940 S | 2/2018 | Goldberg | |
| D835,276 S | 12/2018 | Humphrey | |
| 10,524,922 B2 | 1/2020 | Courtney, Jr. | |
| 2002/0077702 A1 | 6/2002 | Castro | |
| 2003/0134252 A1 | 7/2003 | Sussman | |
| 2003/0187449 A1 | 10/2003 | McCleary | |
| 2003/0204263 A1 | 10/2003 | Justin | |
| 2004/0117027 A1 | 6/2004 | Reiley | |
| 2005/0015093 A1 * | 1/2005 | Suh | A61B 17/1728 606/96 |
| 2005/0038444 A1 | 2/2005 | Binder | |
| 2005/0049709 A1 | 3/2005 | Tornier | |
| 2005/0060039 A1 | 3/2005 | Cyprien | |
| 2005/0222572 A1 | 10/2005 | Chana | |
| 2005/0261775 A1 | 11/2005 | Baum | |
| 2006/0030946 A1 | 2/2006 | Ball | |
| 2006/0069443 A1 | 3/2006 | Deffenbaugh | |
| 2006/0074430 A1 | 4/2006 | Deffenbaugh | |
| 2006/0094958 A1 | 5/2006 | Marquart | |
| 2006/0100637 A1 * | 5/2006 | Rathbun | A61B 17/1728 606/96 |
| 2006/0111787 A1 | 5/2006 | Bailie | |
| 2007/0055380 A1 | 3/2007 | Berelsman | |

(56) References Cited

U.S. PATENT DOCUMENTS

| | | |
|---|---|---|
| 2007/0142917 A1 | 6/2007 | Roche |
| 2007/0219637 A1 | 9/2007 | Berelsman |
| 2007/0219638 A1 | 9/2007 | Jones |
| 2008/0058948 A1 | 3/2008 | Biegun |
| 2008/0109000 A1 | 5/2008 | Maroney |
| 2008/0147070 A1 | 6/2008 | Michel |
| 2008/0188855 A1 | 8/2008 | Brown |
| 2008/0287952 A1 | 11/2008 | Mcminn |
| 2008/0294266 A1 | 11/2008 | Steinberg |
| 2009/0005798 A1 | 1/2009 | Brunner |
| 2009/0018664 A1 | 1/2009 | Kropf |
| 2009/0138016 A1 | 5/2009 | Berthusen |
| 2009/0192621 A1 | 7/2009 | Winslow |
| 2009/0226068 A1 | 9/2009 | Fitz |
| 2009/0228114 A1 | 9/2009 | Clark |
| 2009/0240333 A1 | 9/2009 | Trudeau |
| 2009/0312839 A1 | 12/2009 | Scheker |
| 2010/0049327 A1 | 2/2010 | Isch |
| 2010/0087876 A1 | 4/2010 | Gunther |
| 2010/0087877 A1 | 4/2010 | Gunther |
| 2010/0094429 A1 | 4/2010 | Otto |
| 2010/0161065 A1 | 6/2010 | Williams, Jr. |
| 2010/0228352 A1 | 9/2010 | Courtney, Jr. |
| 2010/0241235 A1 | 9/2010 | Basamania |
| 2010/0268239 A1 | 10/2010 | Sikora |
| 2011/0098710 A1 | 4/2011 | Spratt |
| 2011/0106266 A1 | 5/2011 | Schwyzer |
| 2011/0144760 A1 | 6/2011 | Wong |
| 2011/0190898 A1 | 8/2011 | Lenz |
| 2011/0230972 A1 | 9/2011 | Katrana |
| 2011/0276144 A1 | 11/2011 | Wirth |
| 2012/0130500 A1 | 5/2012 | Maroney |
| 2012/0209392 A1 | 8/2012 | Angibaud |
| 2012/0221112 A1 | 8/2012 | Lappin |
| 2012/0239156 A1 | 9/2012 | De Wilde |
| 2012/0310360 A1 | 12/2012 | Parrott |
| 2012/0330429 A1 | 12/2012 | Axelson, Jr. |
| 2013/0024000 A1 | 1/2013 | Bojarski |
| 2013/0090737 A1 | 4/2013 | Flaherty |
| 2013/0144393 A1 | 6/2013 | Mutchler |
| 2013/0166033 A1 | 6/2013 | Gunther |
| 2013/0190827 A1 | 7/2013 | Butters |
| 2013/0204254 A1 | 8/2013 | Slone et al. |
| 2013/0309030 A1 | 11/2013 | Winslow |
| 2014/0128983 A1 | 5/2014 | Flaherty |
| 2014/0163565 A1 | 6/2014 | Bollinger |
| 2014/0257495 A1 | 9/2014 | Goldberg |
| 2015/0119891 A1 | 4/2015 | Goldberg |
| 2015/0320567 A1 | 11/2015 | Terrill |
| 2015/0335440 A1 | 11/2015 | Linares |
| 2016/0089164 A1 | 3/2016 | Winslow |
| 2016/0095607 A1 | 4/2016 | Hernandez |
| 2016/0143637 A1 | 5/2016 | Nering |
| 2016/0242921 A1 | 8/2016 | Walch |
| 2016/0287266 A1 | 10/2016 | Sikora |
| 2017/0014238 A1 | 1/2017 | Reubelt |
| 2017/0042689 A1 | 2/2017 | Goldberg |
| 2017/0151061 A1 | 6/2017 | Lavi |
| 2017/0231642 A1 | 8/2017 | Chaney |
| 2017/0239058 A1 | 8/2017 | Goldberg |
| 2017/0273795 A1 | 9/2017 | Neichel |
| 2017/0319348 A1 | 11/2017 | Goldberg |
| 2018/0028323 A1 | 2/2018 | Servidio |
| 2018/0200068 A1 | 7/2018 | Goldberg |
| 2018/0303619 A1 | 10/2018 | Kehres |
| 2019/0350717 A1 | 11/2019 | Tuttle |
| 2020/0038194 A1 | 2/2020 | Kester |

FOREIGN PATENT DOCUMENTS

| | | |
|---|---|---|
| AU | 2015204637 | 8/2016 |
| CA | 2821529 | 1/2014 |
| CA | 2941440 | 10/2014 |
| CA | 2972664 | 7/2015 |
| CN | 101442961 | 11/2012 |
| CN | 102014800 | 4/2014 |
| CN | 105377195 | 3/2016 |
| CN | 106132355 | 11/2016 |
| DE | 10130796 | 1/2003 |
| DE | 10134511 | 2/2003 |
| EP | 1518519 | 3/2005 |
| EP | 1159939 | 7/2005 |
| EP | 2238949 | 10/2010 |
| EP | 2446859 | 5/2012 |
| EP | 2559406 | 2/2013 |
| EP | 2689751 | 1/2014 |
| EP | 2967892 | 1/2016 |
| EP | 3091940 | 11/2016 |
| EP | 3284442 | 2/2018 |
| FR | 2825263 | 12/2002 |
| FR | 2836821 | 5/2004 |
| GB | 2308068 | 9/1999 |
| IN | 201508960 | 7/2016 |
| IN | 201617026041 | 8/2016 |
| WO | WO1998015241 | 4/1998 |
| WO | WO2000018335 | 4/2000 |
| WO | WO2002017822 | 3/2002 |
| WO | WO2006110896 | 10/2006 |
| WO | WO2007109800 | 9/2007 |
| WO | WO2009108591 | 9/2009 |
| WO | WO2011029911 | 3/2011 |
| WO | WO2012030794 | 3/2012 |
| WO | WO2013020026 | 2/2013 |
| WO | WO2014005644 | 1/2014 |
| WO | WO2014164265 | 10/2014 |
| WO | WO2015106136 | 7/2015 |
| WO | WO2018017615 | 1/2018 |

\* cited by examiner

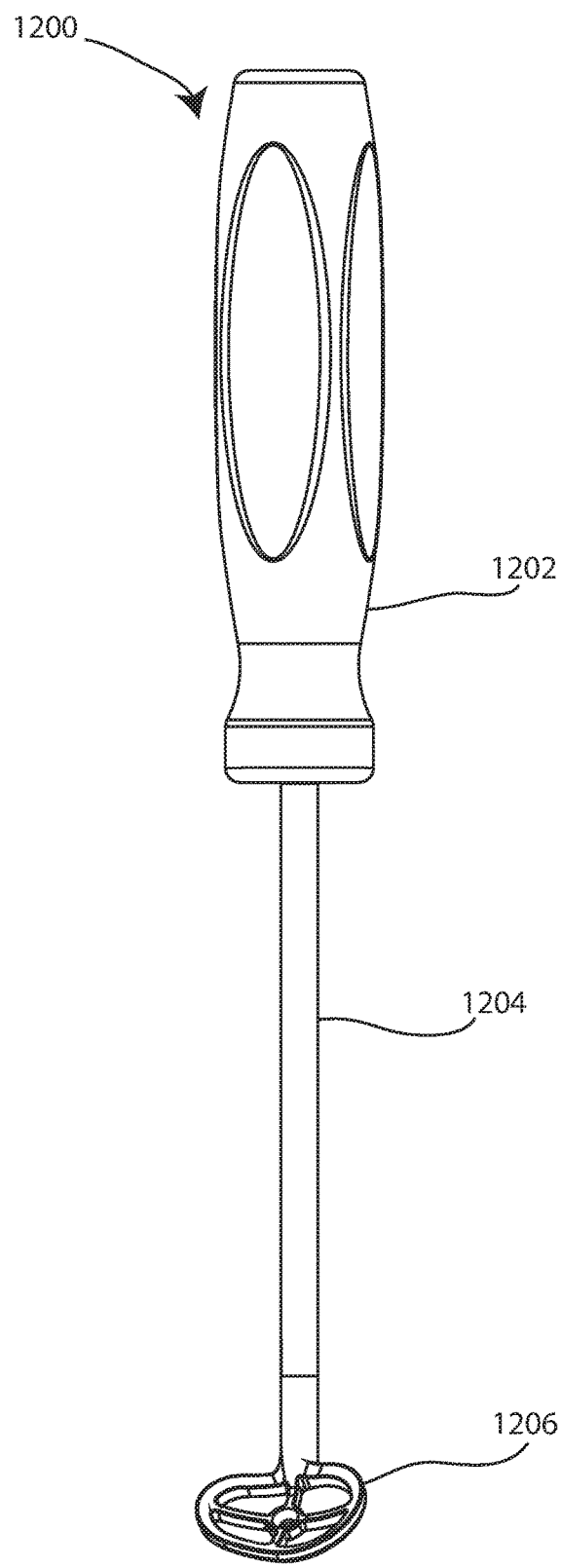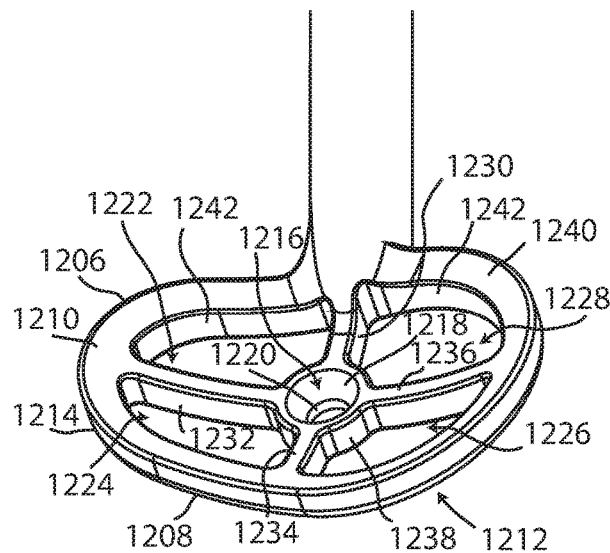
Fig. 8A
Fig. 8B

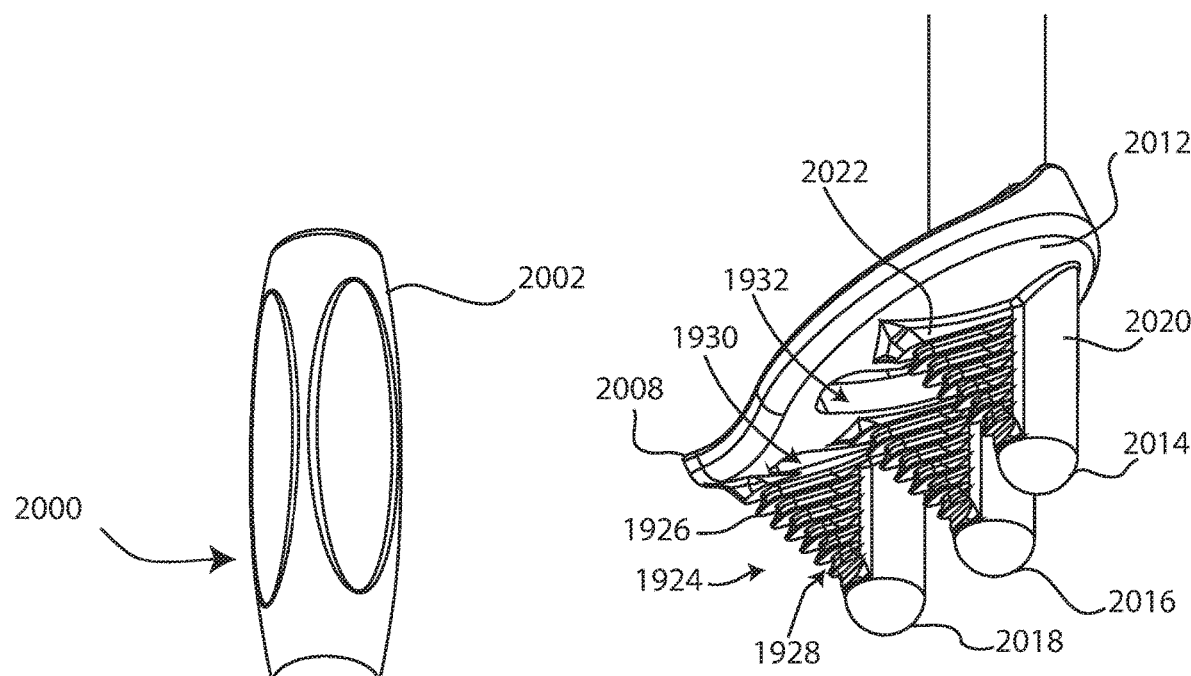
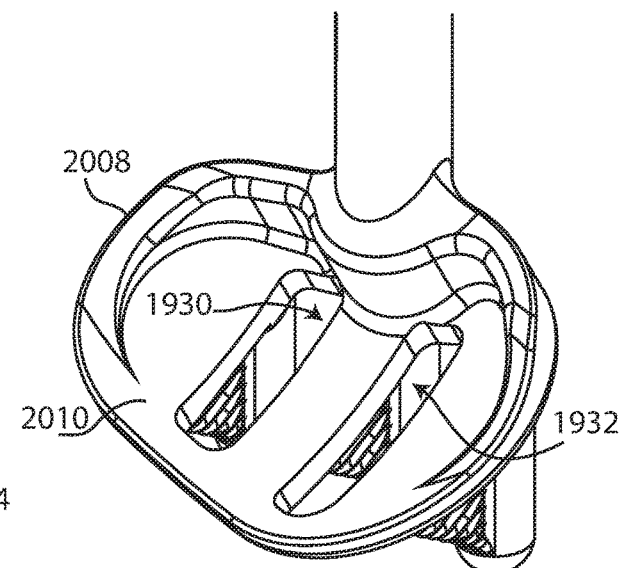
Fig. 16B
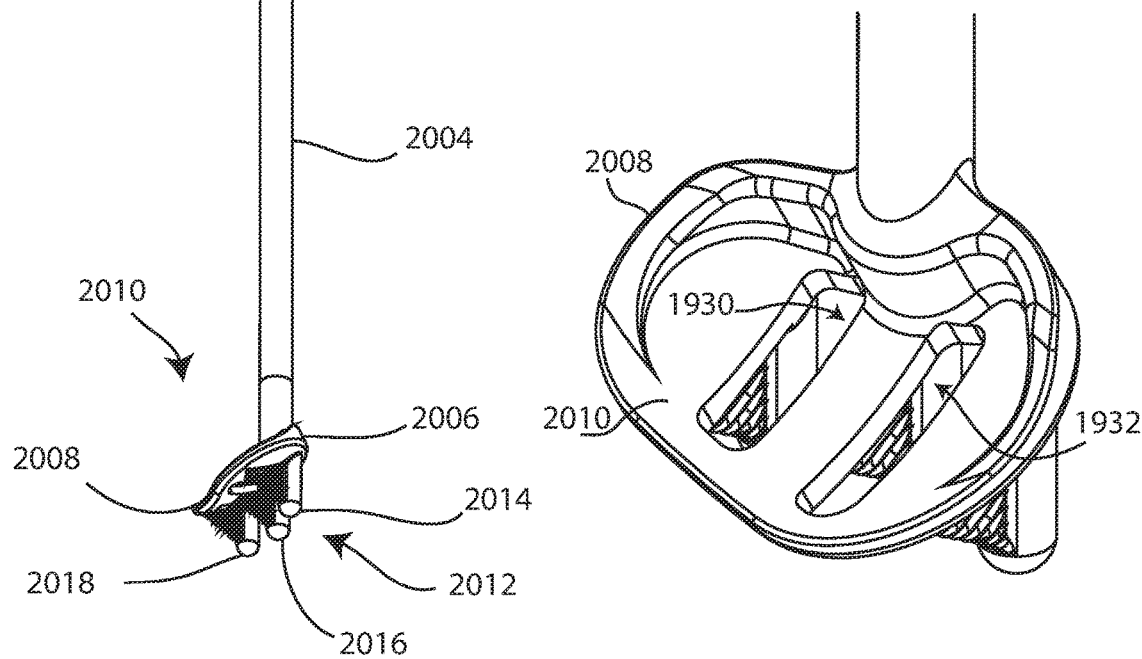
Fig. 16A  Fig. 16C

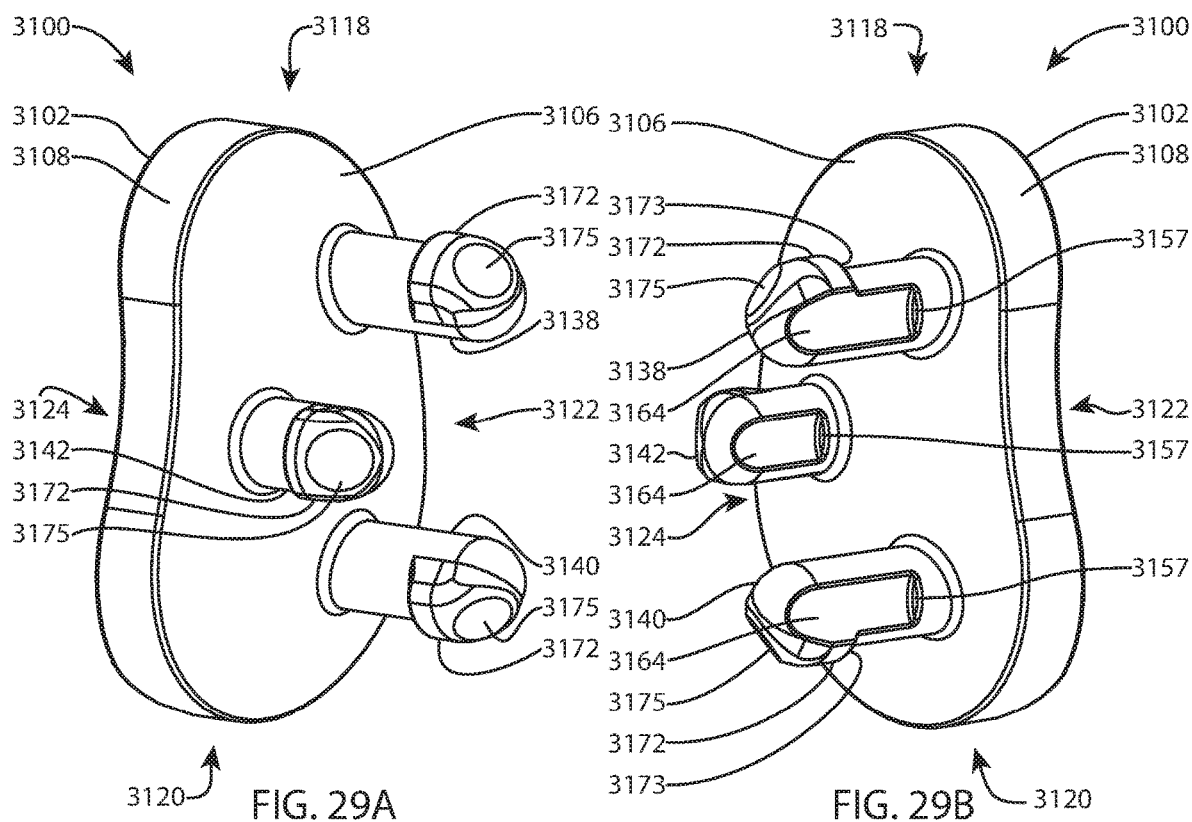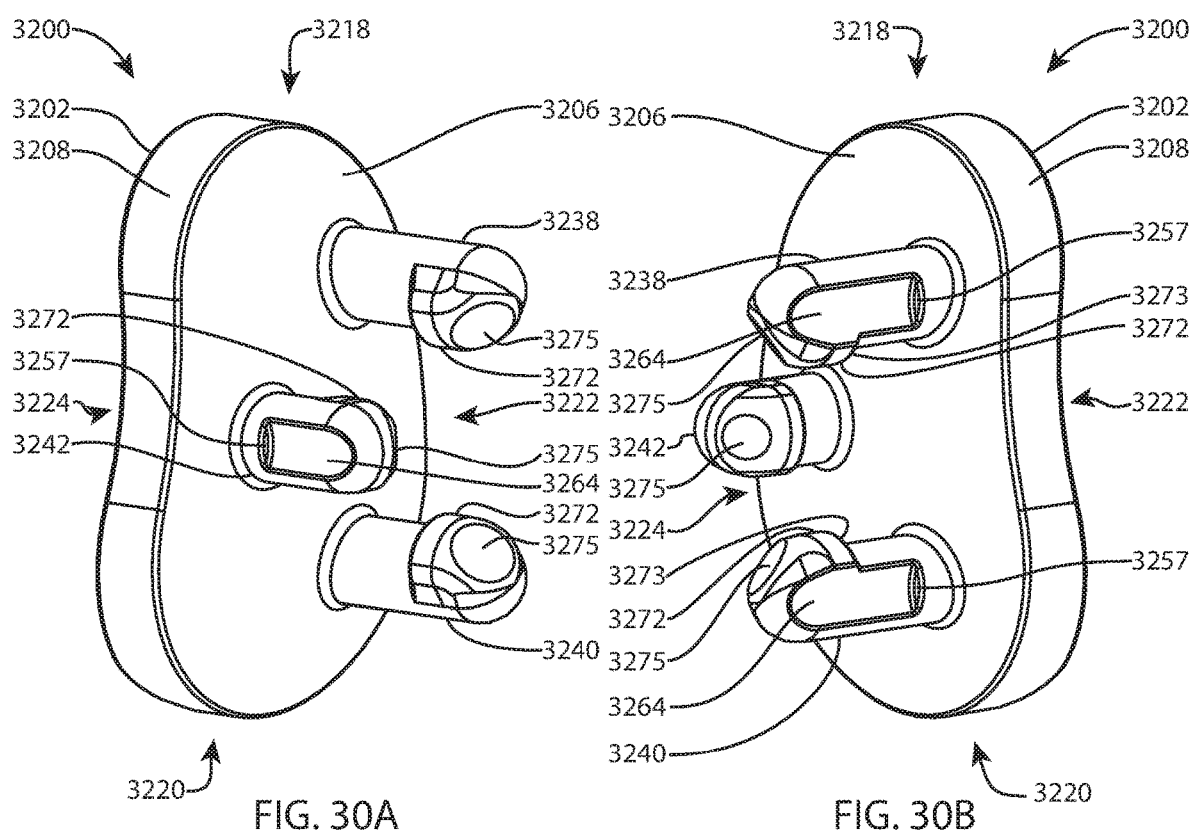

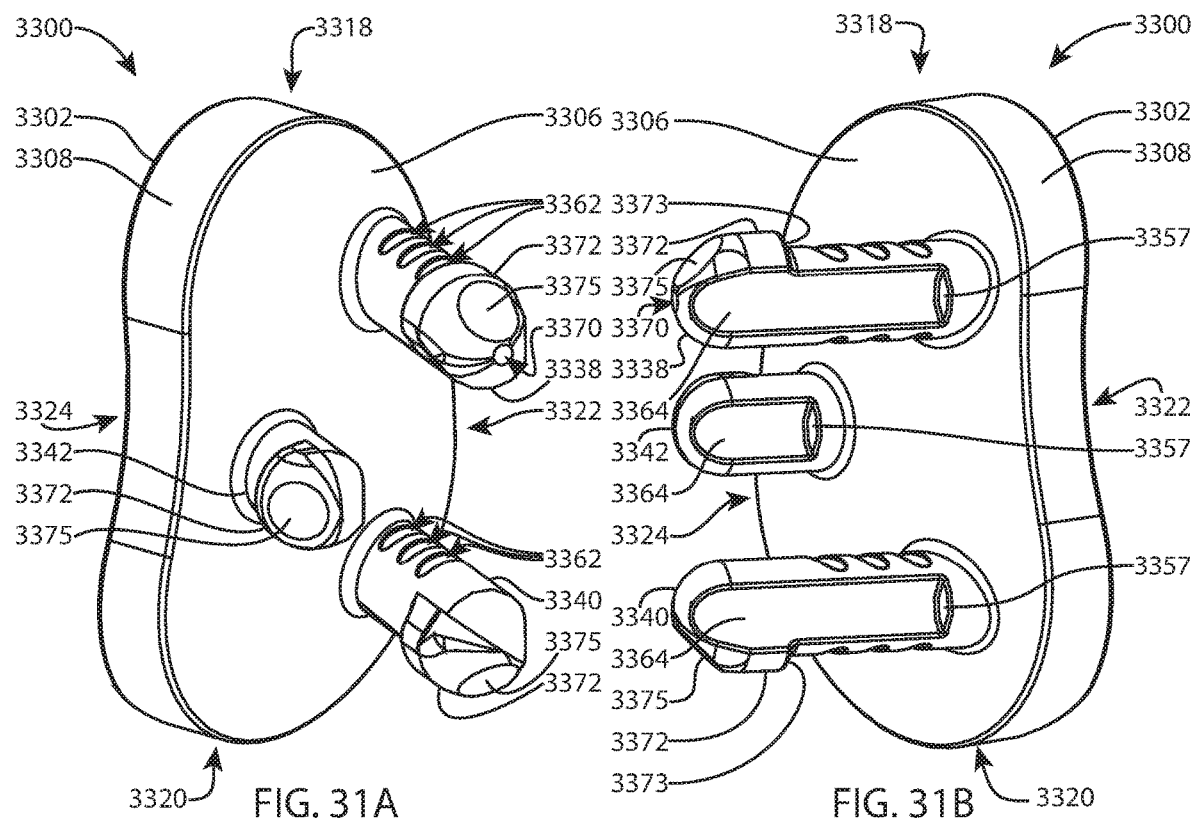
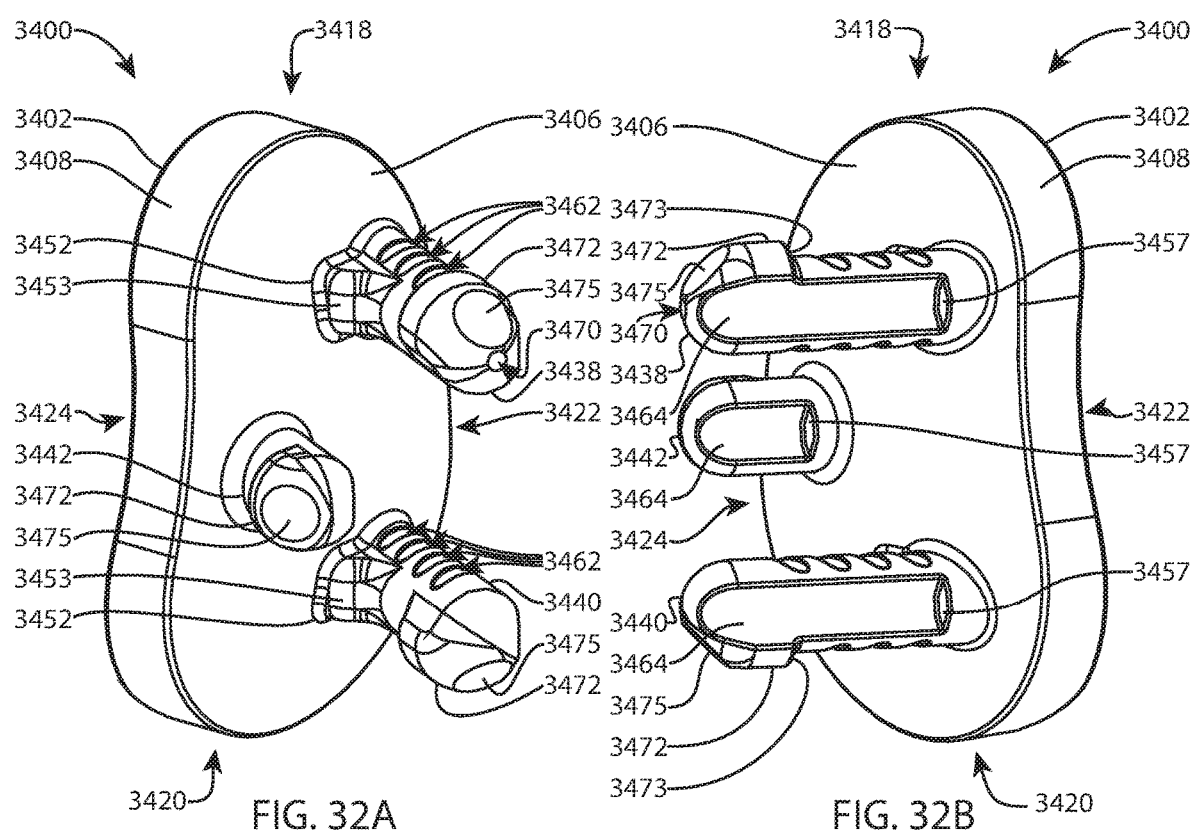

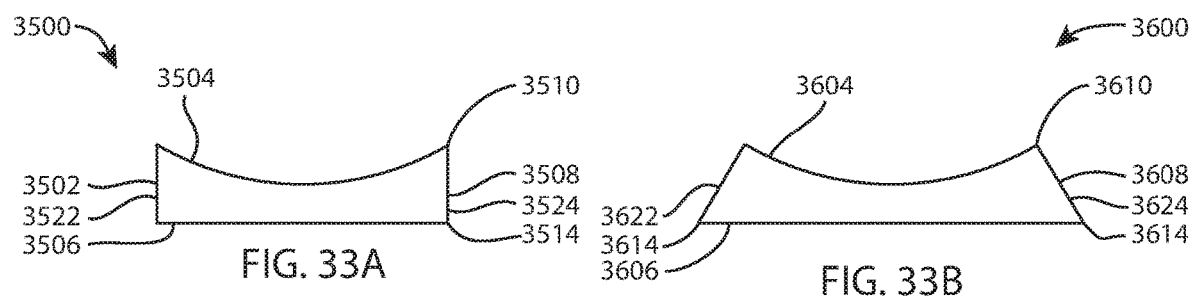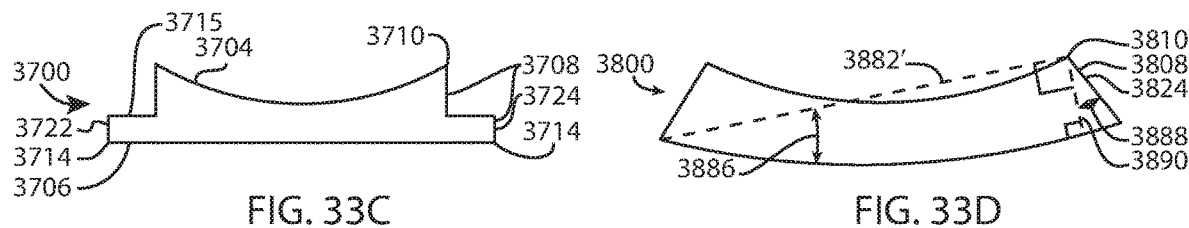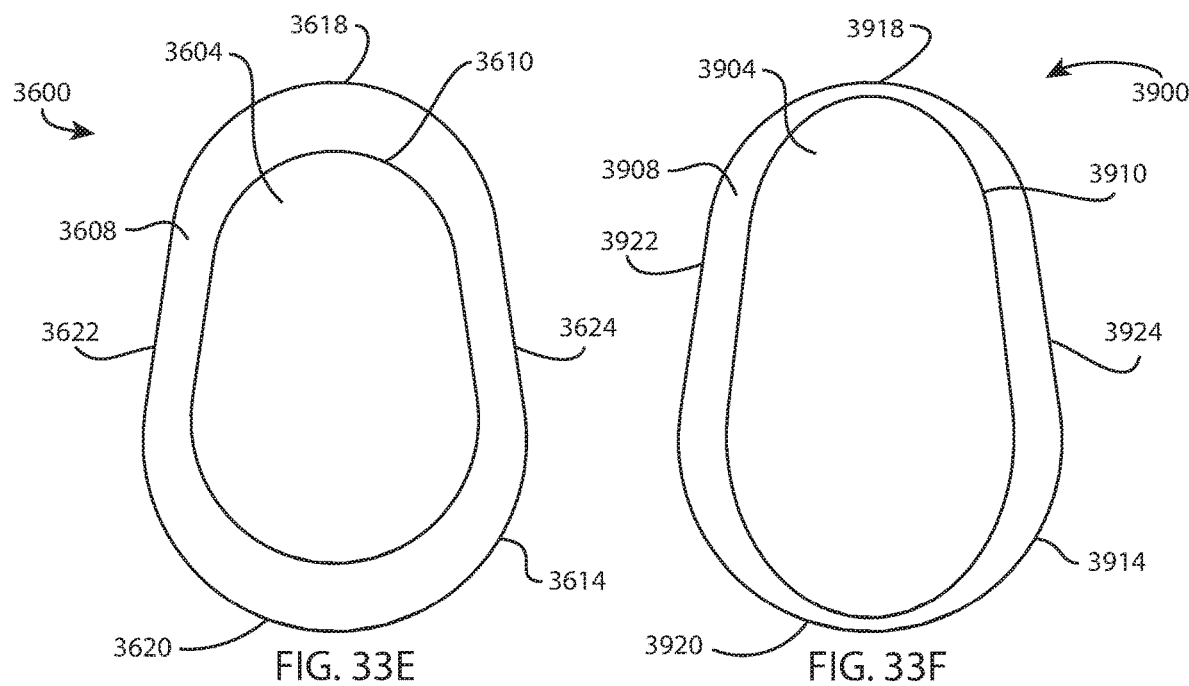

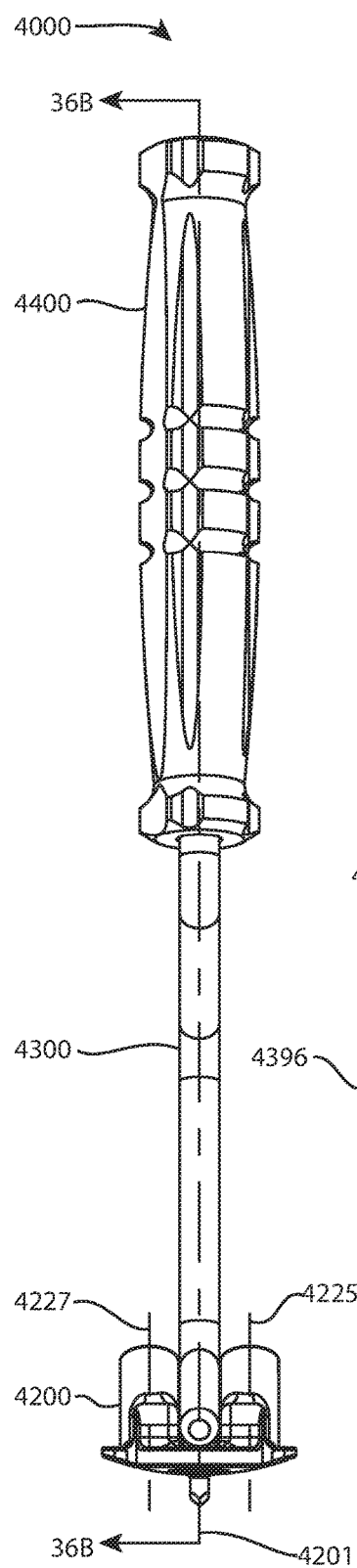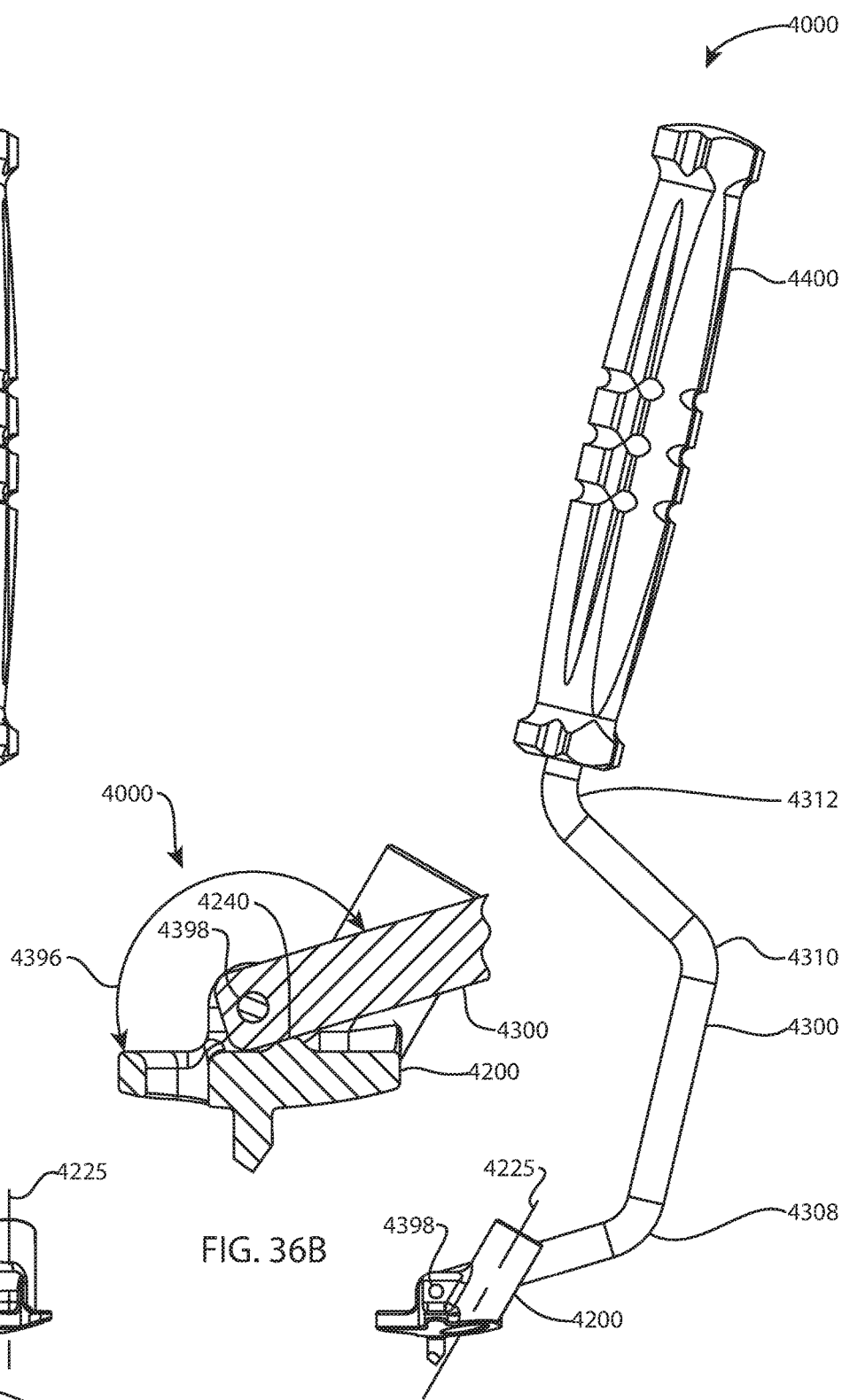
FIG. 36A  FIG. 36B  FIG. 37

STABILIZED DRILL GUIDE

CROSS-REFERENCE TO RELATED APPLICATIONS

The present application claims the benefit of:

U.S. Provisional Patent Application No. 62/367,533, Attorney's Docket No. CAO-6 PROV, entitled STABILIZED DRILL GUIDE, which was filed on Jul. 27, 2016.

The present application is also a continuation-in-part of:

U.S. patent application Ser. No. 14/042,258, Attorney's Docket No. CAO-1, entitled GLENOID ARTHROPLASTY, which was filed on Sep. 30, 2013;

U.S. patent application Ser. No. 15/587,895, Attorney's Docket No. CAO-1 CON1, entitled GLENOID ARTHROPLASTY, which was filed on May 5, 2017;

U.S. patent application Ser. No. 14/592,837, Attorney's Docket No. CAO-1 CIP1, entitled GLENOID ARTHROPLASTY AND OFFSET REAMERS, which was filed on Jan. 8, 2015;

U.S. patent application Ser. No. 15/228,443, Attorney's Docket No. CAO-4, entitled GLENOID ARTHROPLASTY WITH MULTI-DIRECTIONAL FIXATION, which was filed on Aug. 4, 2016; and U.S. patent application Ser. No. 15/653,305, Attorney's Docket No. CAO-4 CIP1, entitled ARTHROPLASTY PROSTHESES WITH MULTI-AXIS FIXATION, which was filed on Jul. 18, 2017.

U.S. patent application Ser. No. 14/042,258 claims the benefit of:

U.S. Provisional Patent Application No. 61/776,398, Attorney's Docket No. 3858U.001, entitled OBLIQUE-INSERTION ANCHORING MECHANISM FOR GLENOID PROSTHETIC COMPONENT, which was filed on Mar. 11, 2013.

U.S. patent application Ser. No. 15/587,895 is a continuation of U.S. patent application Ser. No. 14/042,258.

U.S. patent application Ser. No. 14/592,837 claims the benefit of:

U.S. Provisional Patent Application No. 61/925,893, Attorney's Docket No. CAO-3 PROV, entitled OFFSET REAMERS, which was filed on Jan. 10, 2014.

U.S. patent application Ser. No. 14/592,837 is also a continuation-in-part of U.S. patent application Ser. No. 14/042,258.

U.S. patent application Ser. No. 15/228,443 claims the benefit of:

U.S. Provisional Patent Application No. 62/203,255, Attorney's Docket No. CAO-4 PROV, entitled GLENOID ARTHROPLASTY WITH MULTI-DIRECTIONAL FIXATION, which was filed on Aug. 10, 2015.

U.S. patent application Ser. No. 15/653,305 claims the benefit of:

U.S. Provisional Patent Application No. 62/363,607, Attorney's Docket No. CAO-5 PROV, entitled ARTHROPLASTY PROSTHESES WITH MULTI-AXIS FIXATION, which was filed on Jul. 18, 2016.

U.S. patent application Ser. No. 15/653,305 is also a continuation-in-part of U.S. patent application Ser. No. 15/228,443.

The foregoing are incorporated by reference as though set forth herein in their entirety.

TECHNICAL FIELD

The present disclosure relates to a drill guide for use in surgery. More specifically, the present disclosure relates to a drill guide for orthopedic surgery, such as glenoid arthroplasty. One of skill in the art will appreciate that the principles set forth herein are applicable to other types of surgery where a drill guide is used.

BACKGROUND

Orthopedic implants are designed to be rigidly fixed within bone, both with and without the use of bone cement. It is imperative than the implants are seated within bone in channels that precisely match the actual shape of the implants in order for them to lie flat or otherwise seat in the way to minimize chance of failure. If the channels created for the implant to seat are in an improper position, orientation, size, or incorrect depth, the implant may not seat correctly, and may be prone to abnormal forces, loosening, or may not function properly.

Loosening of an implanted orthopedic device can cause pain, loss of motion and further tissue destruction, possibly leading to the implant needing to be removed or revised. Reoperation for loose orthopedic implants is a major source of increased costs to the healthcare system. Therefore it is important that implants are implanted precisely the way they were engineered to be placed in order maximize the chance of success.

SUMMARY

The various systems and methods of the present technology have been developed in response to the present state of the art, and in particular, in response to the problems and needs in the art that have not yet been fully solved by currently available drill guides. The systems and methods of the present technology may provide meaningful improvement in the stability of the drill guide working portion, thereby improving the accuracy of the prepared bone socket, thereby improving the implanted position of the corresponding prosthesis (to be closer to the nominal design implant position).

To achieve the foregoing, and in accordance with the technology as embodied and broadly described herein, an aspect of the technology includes a drill guide including: a working portion including a bone-facing side, an opposite obverse side, and a through hole that extends through at least a portion of the working portion, wherein the through hole receives a drill with clearance; and a shaft coupled to the working portion by a joint, wherein the shaft is movable relative to the working portion about the joint.

Embodiments of this aspect may include one or more of the following attributes. The joint is selected from the group consisting of a hinge joint, a universal joint, a ball-and-socket joint, a polyaxial joint, a saddle joint, a flexible shaft portion, and a magnetic joint. The joint is a hinge joint between the shaft and the working portion. The working portion is captive to the shaft. The shaft is movable relative to the working portion about the joint while the drill is actuated in the through hole. The shaft is movable relative to the working portion about the joint within a range of motion, wherein the obverse side includes at least one range of motion stop associated with the joint. The drill guide includes a biasing element that biases the shaft to contact the at least one range of motion stop. The biasing element is selected from the group consisting of a spring, a magnet, a cam, and a drag pin. The at least one range of motion stop includes a ridge on the obverse side, wherein the shaft contacts the ridge at a first end of the range of motion. The drill guide includes a locking mechanism including a first setting and a second setting; wherein when the locking mechanism is in the first setting, the shaft is immobilized relative to the working portion; wherein when the locking mechanism is in the second setting, the shaft is freely movable relative to the working portion. The bone-facing side includes a stabilizing feature that stabilizes the working portion relative to a bone. The stabilizing feature includes a spike protruding from the bone-facing side. The working portion includes at least one anatomical reference feature. The working portion includes a pair of outwardly extending anatomical reference tabs on opposite sides of the working portion. When the bone-facing side is placed against a glenoid socket, the working portion is positionable so that the pair of outwardly extending anatomical reference tabs are aligned along a superior-inferior direction.

Another aspect of the technology includes a drill guide including: a working portion including a through hole, wherein the through hole receives a drill with clearance; and a handle portion coupled to the working portion by a joint, wherein the handle portion is movable relative to the working portion about the joint.

Embodiments of this aspect may include one or more of the following attributes. The joint is selected from the group consisting of a hinge joint, a universal joint, a ball-and-socket joint, a polyaxial joint, a saddle joint, a flexible shaft portion, and a magnetic joint. The joint is a hinge joint between the handle portion and the working portion. The working portion is captive to the handle portion. The handle portion is movable relative to the working portion about the joint while the drill is actuated in the through hole. The handle portion is movable relative to the working portion about the joint within a range of motion, wherein the obverse side includes at least one range of motion stop associated with the joint. The drill guide includes a biasing element that biases the handle portion to contact the at least one range of motion stop. The biasing element is selected from the group consisting of a spring, a magnet, a cam, and a drag pin. The at least one range of motion stop includes a ridge on the obverse side, wherein the handle portion contacts the ridge at a first end of the range of motion. The drill guide includes a locking mechanism including a first setting and a second setting; wherein when the locking mechanism is in the first setting, the handle portion is immobilized relative to the working portion; wherein when the locking mechanism is in the second setting, the handle portion is freely movable relative to the working portion. The working portion includes a bone-facing side includes a stabilizing feature that stabilizes the working portion relative to a bone. The stabilizing feature includes a spike protruding from the bone-facing side. The working portion includes at least one anatomical reference feature. The working portion includes a pair of outwardly extending anatomical reference tabs on opposite sides of the working portion. When the bone-facing side is placed against a glenoid socket, the working portion is positionable so that the pair of outwardly extending anatomical reference tabs are aligned along a superior-inferior direction.

Yet another aspect of the technology includes a drill guide including: a working portion including a through hole and a first joint portion, wherein the through hole receives a drill with clearance; and a handle portion including a second joint portion, wherein the handle portion is coupled to the working portion by a joint formed by the first and second joint portions, wherein the handle portion is movable relative to the working portion about the joint.

Embodiments of this aspect may include one or more of the following attributes. The joint is selected from the group consisting of a hinge joint, a universal joint, a ball-and-socket joint, a polyaxial joint, a saddle joint, a flexible shaft portion, and a magnetic joint. The joint is a hinge joint between the handle portion and the working portion. The working portion is captive to the handle portion. The handle portion is movable relative to the working portion about the joint while the drill is actuated in the through hole. The handle portion is movable relative to the working portion about the joint within a range of motion, wherein the obverse side includes at least one range of motion stop associated with the joint. The drill guide includes a biasing element that biases the handle portion to contact the at least one range of motion stop. The biasing element is selected from the group consisting of a spring, a magnet, a cam, and a drag pin. The at least one range of motion stop includes a ridge on the obverse side, wherein the handle portion contacts the ridge at a first end of the range of motion. The drill guide includes a locking mechanism including a first setting and a second setting; wherein when the locking mechanism is in the first setting, the handle portion is immobilized relative to the working portion; wherein when the locking mechanism is in the second setting, the handle portion is freely movable relative to the working portion. The working portion includes a bone-facing side includes a stabilizing feature that stabilizes the working portion relative to a bone. The stabilizing feature includes a spike protruding from the bone-facing side. The working portion includes at least one anatomical reference feature. The working portion includes a pair of outwardly extending anatomical reference tabs on opposite sides of the working portion. When the bone-facing side is placed against a glenoid socket, the working portion is positionable so that the pair of outwardly extending anatomical reference tabs are aligned along a superior-inferior direction.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 8A is an isometric view of a size template; and FIG. 8B is a detail view of a working portion of the size template of FIG. 8A;

FIG. 16A is an isometric view of a broach; FIG. 16B is a detail view of a working portion of the broach of FIG. 16A; and FIG. 16C is another detail view of a working portion of the broach of FIG. 16A from a different direction;

FIG. 29A is a medial-superior-posterior view of yet another glenoid component; and FIG. 29B is a medial-superior-anterior view of the glenoid component of FIG. 29A;

FIG. 30A is a medial-superior-posterior view of yet another glenoid component; and FIG. 30B is a medial-superior-anterior view of the glenoid component of FIG. 30A;

FIG. 31A is a medial-superior-posterior view of yet another glenoid component; and FIG. 31B is a medial-superior-anterior view of the glenoid component of FIG. 31A;

FIG. 32A is a medial-superior-posterior view of yet another glenoid component; and FIG. 32B is a medial-superior-anterior view of the glenoid component of FIG. 32A;

FIG. 33A is a cross section of yet another glenoid component, taken across the anterior-poster width of the glenoid component; FIG. 33B is a cross section of yet another glenoid component, taken across the anterior-poster width of the glenoid component; FIG. 33C is a cross section of yet another glenoid component, taken across the anterior-poster width of the glenoid component; FIG. 33D is a cross section of yet another glenoid component, taken across the anterior-posterior width of the glenoid component; FIG. 33E is a lateral view of the glenoid component of FIG. 33B; and FIG. 33F is a lateral view of yet another glenoid component;

FIG. 36A is a front view of the drill guide of FIG. 34;

FIG. 36B is a cross sectional detail view of a portion of the drill guide of FIG. 34, taken along section line 36B-36B of FIG. 3A;

FIG. 37 is a side view of the drill guide of FIG. 34;

DETAILED DESCRIPTION

Figure 1A:
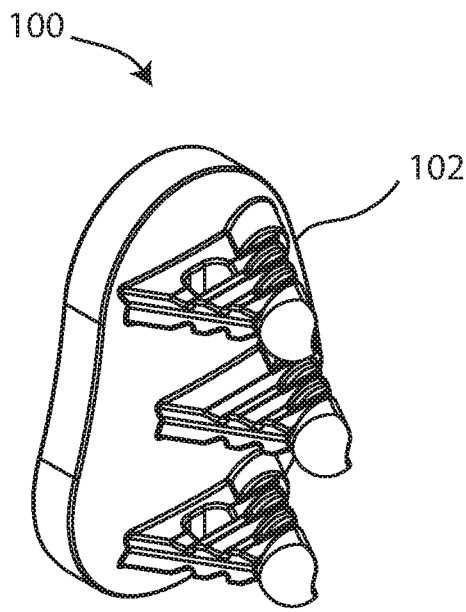
FIG. 1A is a superior-posterior-medial view of a glenoid component.
Figure 1B:
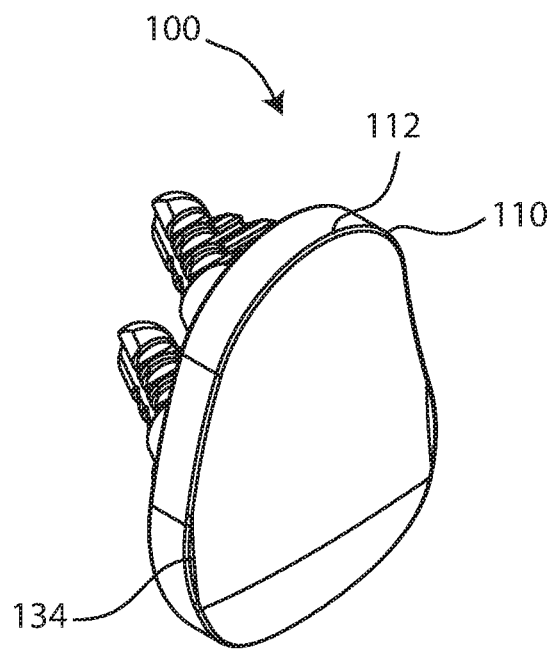
FIG. 1B is a superior-anterior-medial view of the glenoid component of FIG. 1A.
Figure 2A:
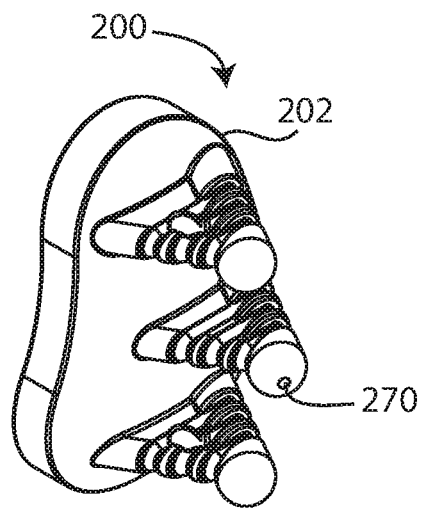
FIG. 2A is a superior-posterior-medial view of another glenoid component.
Figure 2B:
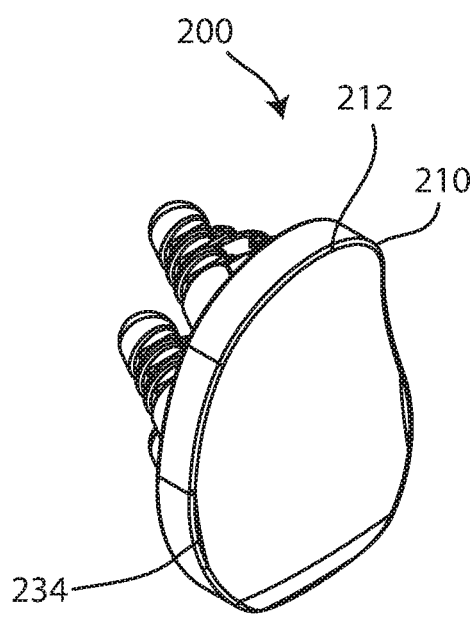
FIG. 2B is a superior-anterior-medial view of the glenoid component of FIG. 2A.
Figure 3A:
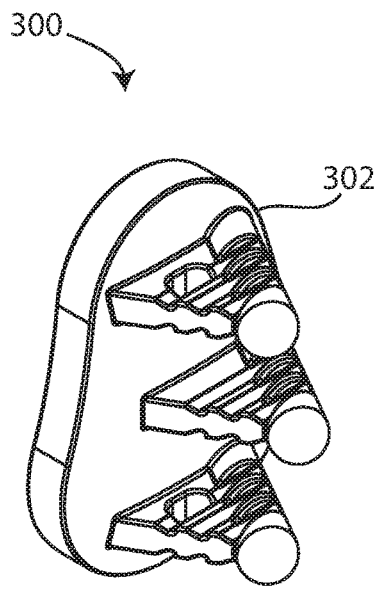
FIG. 3A is a superior-posterior-medial view of yet another glenoid component.
Figure 3B:
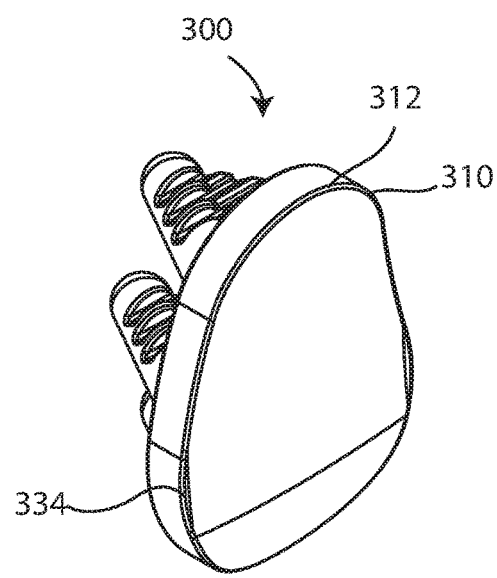
FIG. 3B is a superior-anterior-medial view of the glenoid component of FIG. 3A.
Figure 4:
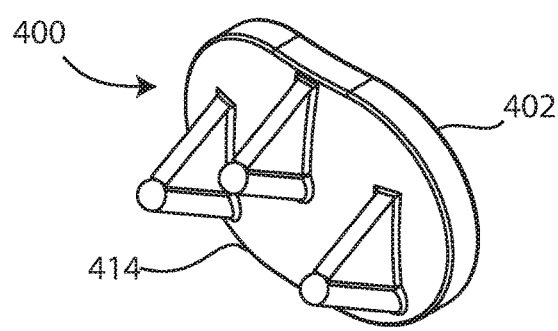
FIG. 4 is a superior-posterior-medial view of yet another glenoid component.
Figure 5:
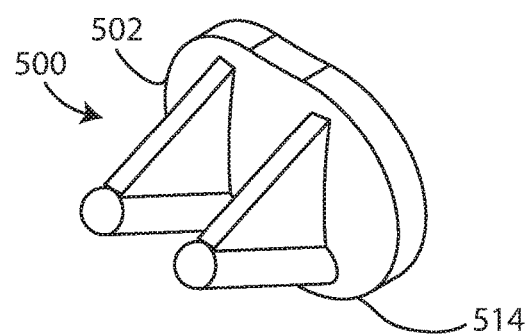
FIG. 5 is a superior-posterior-medial view of yet another glenoid component.
Figure 6:
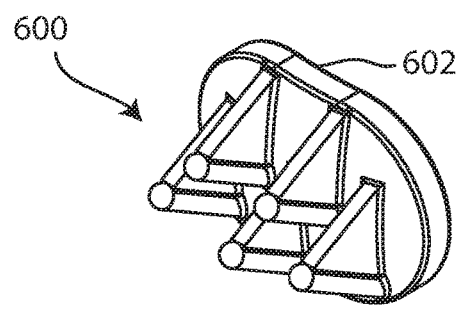
FIG. 6 is a superior-posterior-medial view of yet another glenoid component.
Figure 7A:
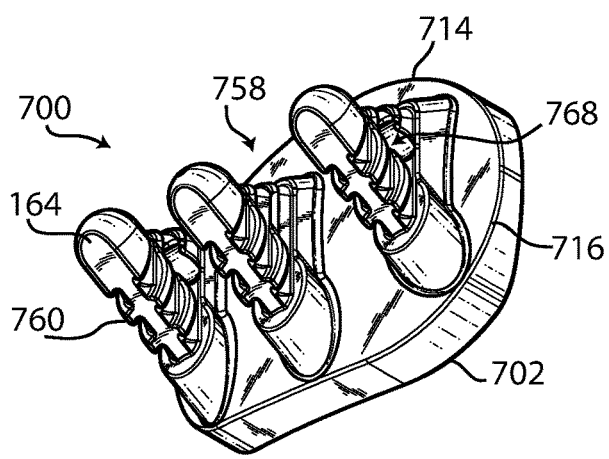
FIG. 7A is an inferior-anterior-medial view of yet another glenoid component.
Figure 7B:
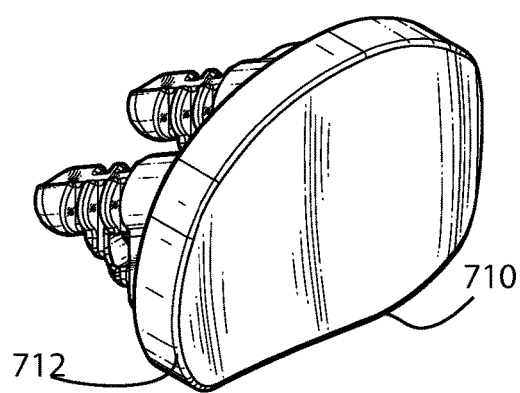
FIG. 7B is a superior-anterior-lateral view of the glenoid component of FIG. 7A.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. A sagittal plane divides a body into right and left portions. A midsagittal plane divides the body into bilaterally symmetric right and left halves. A coronal plane divides a body into anterior and posterior portions. A transverse plane divides a body into superior and inferior portions. The sagittal, coronal, and transverse planes are mutually perpendicular. A scapular plane is parallel to the body of the scapula and normal to the glenoid articular surface; the scapular plane is normally 30 to 45 degrees anterior of the coronal plane. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

The drill guide 4000 disclosed herein may be included in a system with implants and/or other instruments. For example, the illustrated drill guide 4000 is adapted for glenoid arthroplasty and may be included in a system with the implants and/or instruments disclosed at least in the following copending applications: U.S. patent application Ser. No. 14/042,258, filed on Sep. 30, 2013; U.S. patent application Ser. No. 15/587,895, filed on May 5, 2017; U.S. patent application Ser. No. 14/592,837, filed on Jan. 8, 2015; U.S. patent application Ser. No. 15/228,443, filed on Aug. 4, 2016; and U.S. patent application Ser. No. 15/653,305, filed on Jul. 18, 2017. The foregoing are incorporated by reference as though set forth herein in their entirety.

Figure 9A:
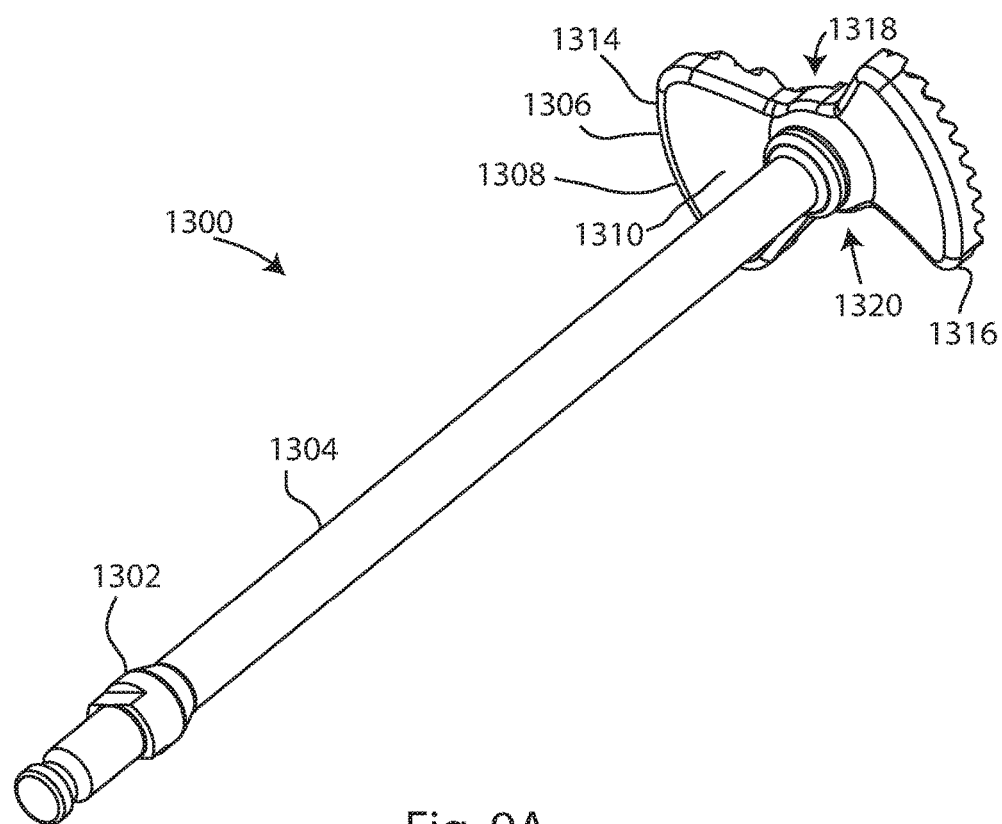
FIG. 9A is an isometric view of a reamer.
Figure 9B:
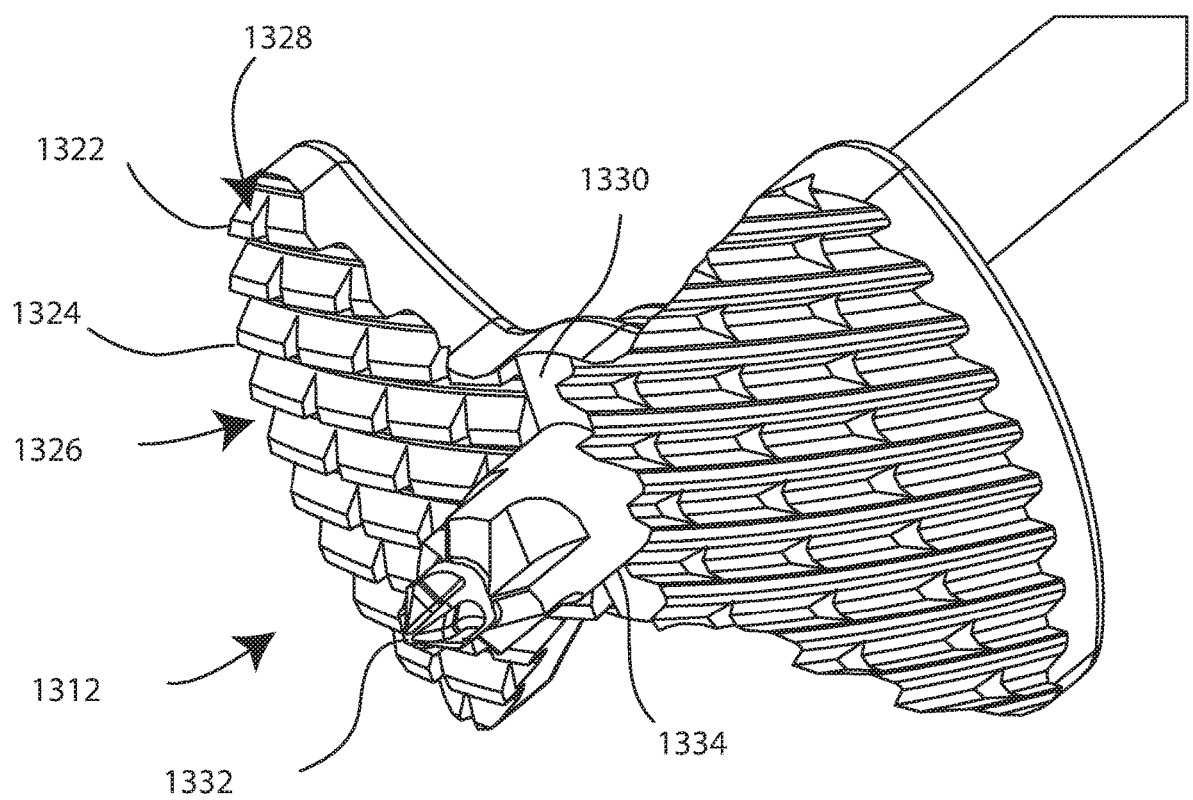
FIG. 9B is another isometric view of the reamer of FIG. 9A from a different direction.
Figure 10A:
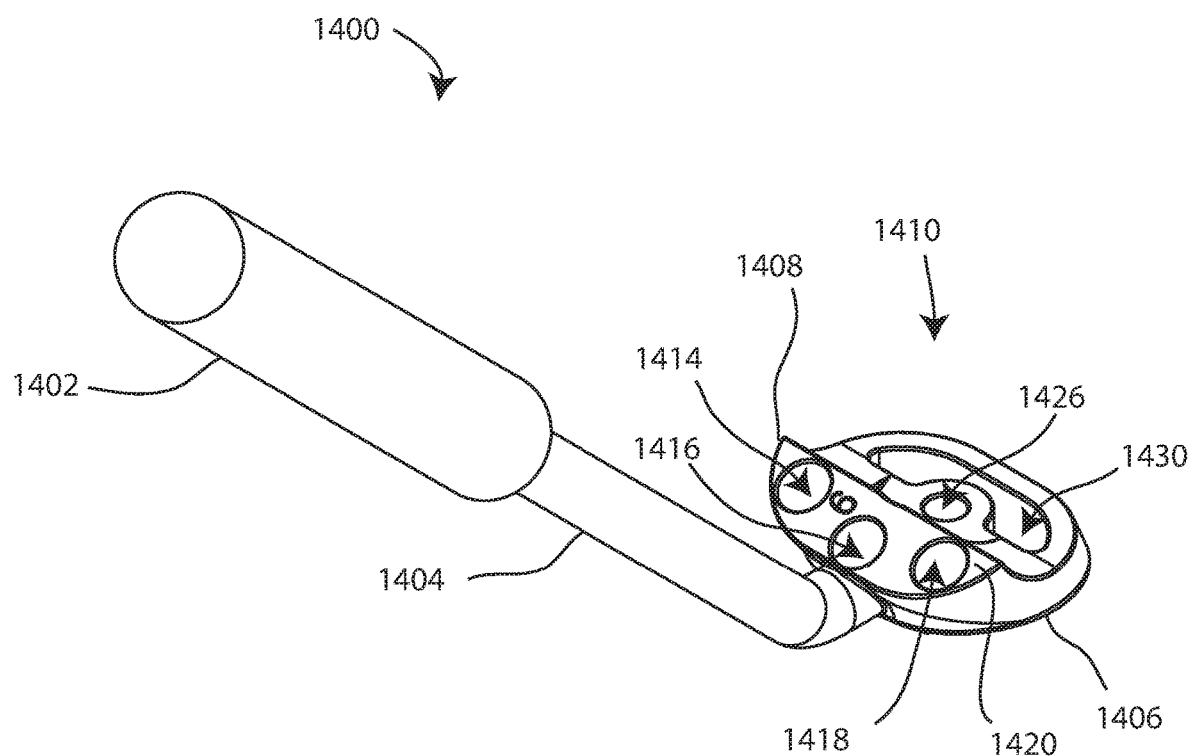
FIG. 10A is an isometric view of a drill guide.
Figure 10B:
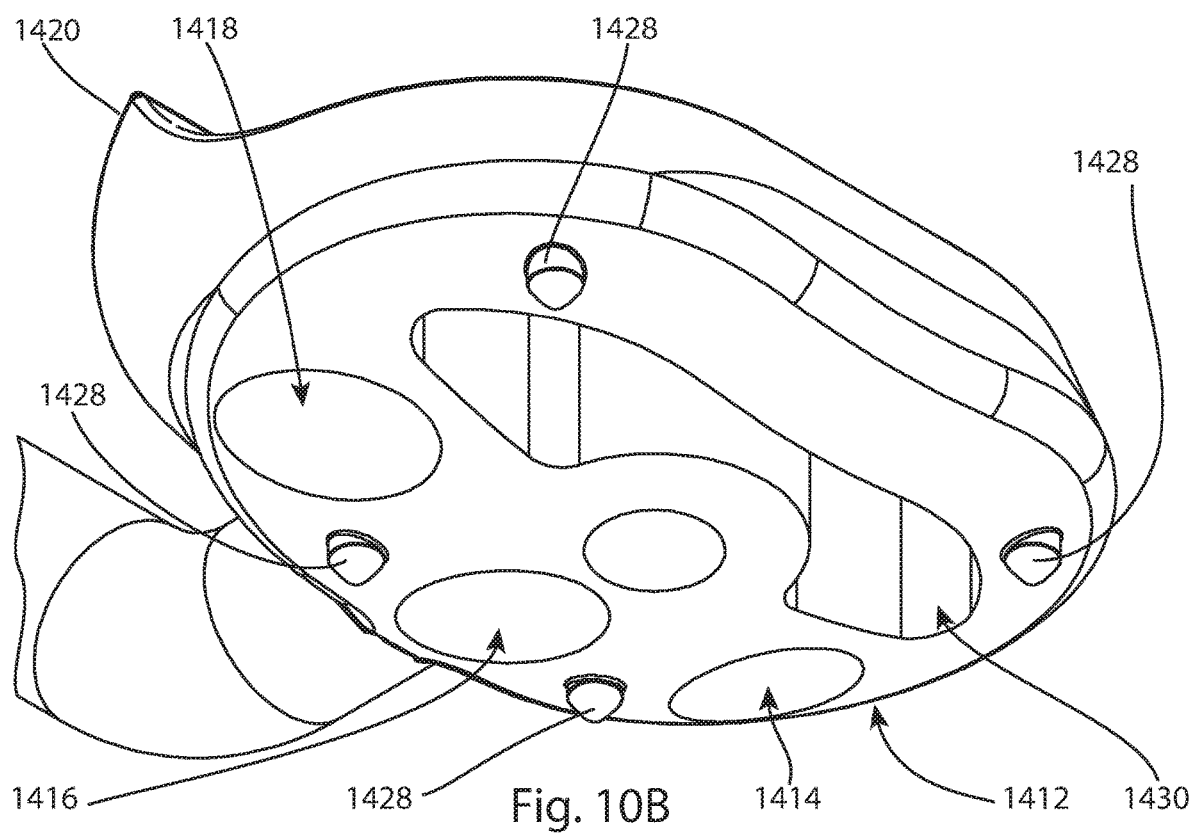
FIG. 10B is another isometric view of the drill guide of FIG. 22A from a different direction.
Figure 11A:
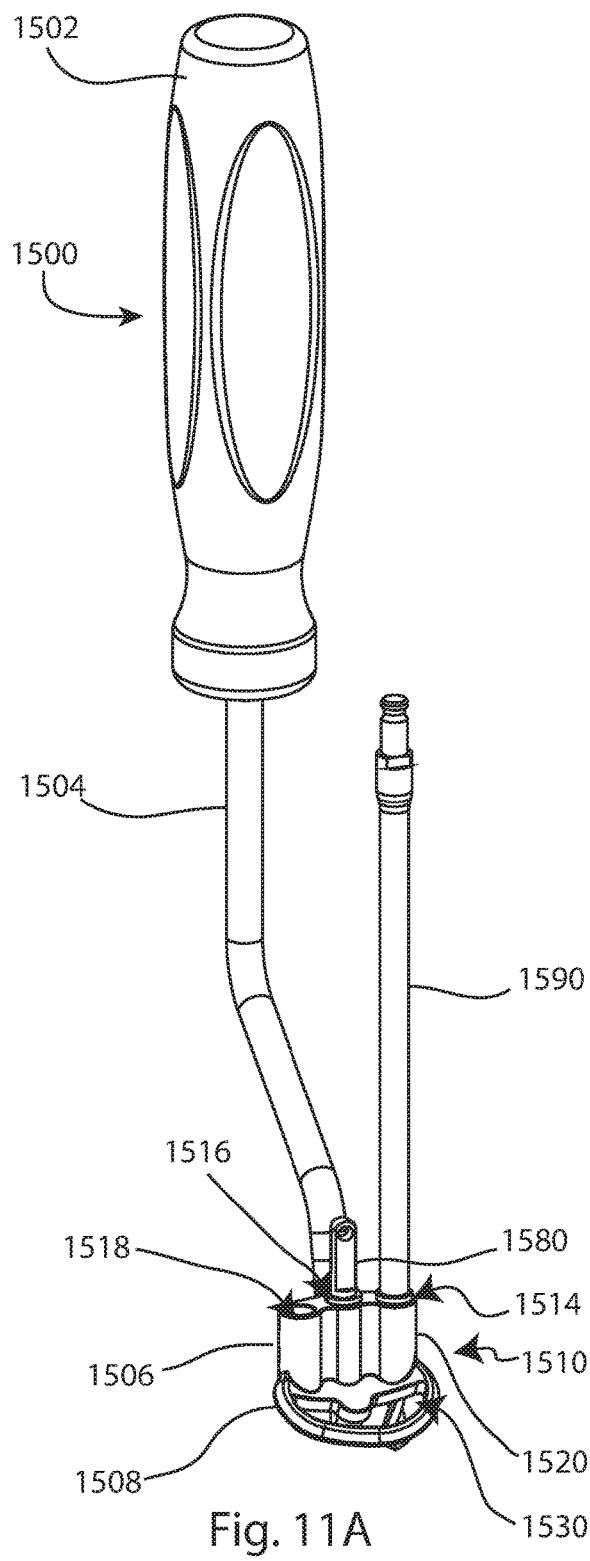
FIG. 11A is an isometric view of another drill guide with a drill and a keel position tamp.
Figure 11B:
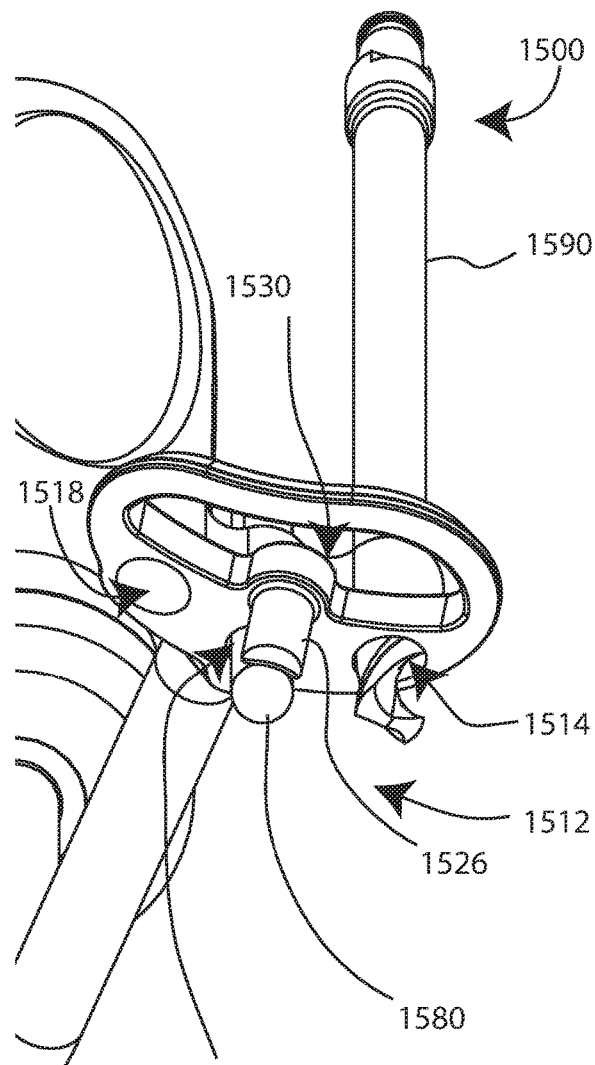
FIG. 11B is another isometric view of the drill guide, drill, and keel position tamp of FIG. 11A from a different direction.
Figure 12A:
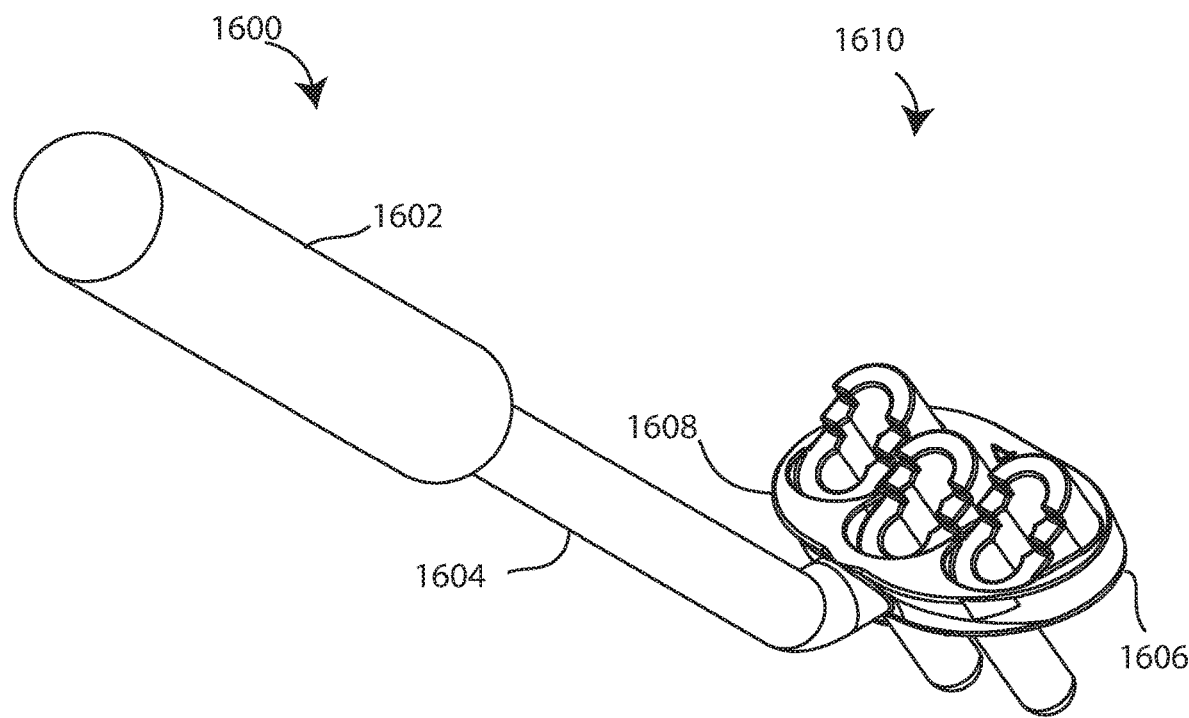
FIG. 12A is an isometric view of yet another drill guide.
Figure 12B:
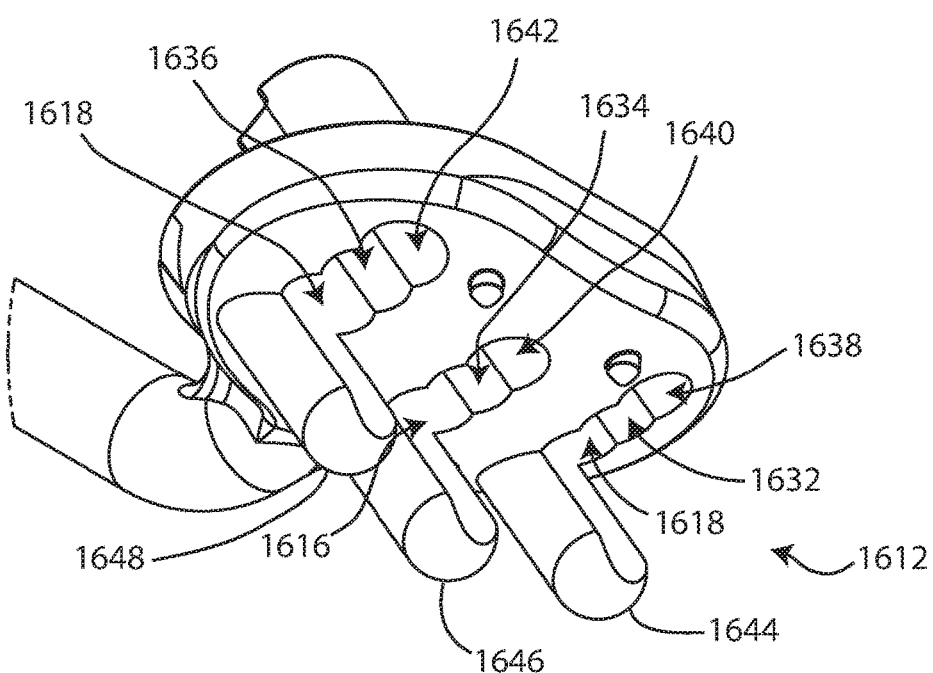
FIG. 12B is an enlarged detail view of a portion of the drill guide of FIG. 12A.
Figures 13A, 13B:
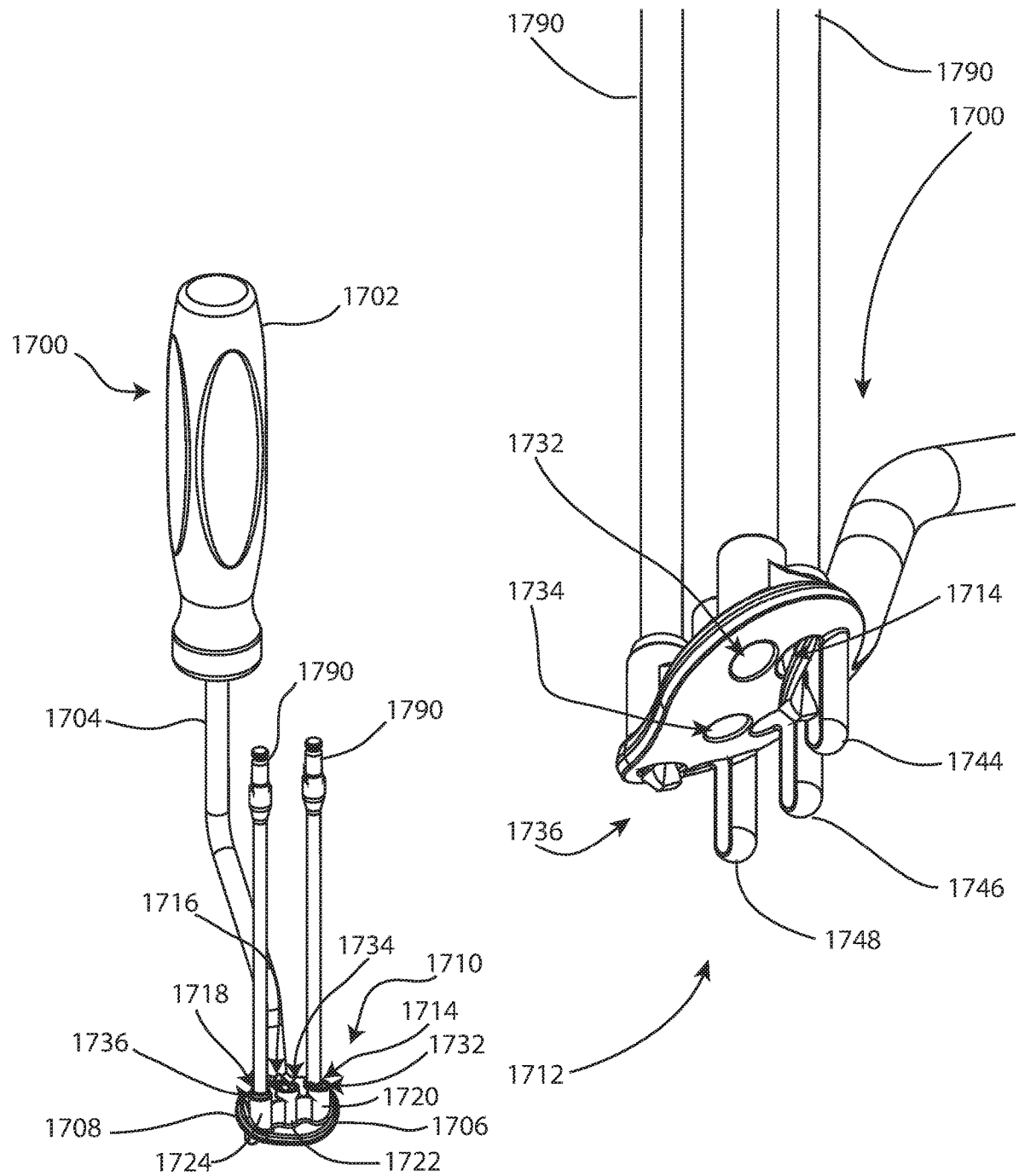
FIG. 13A is an isometric view of yet another drill guide with drills.
FIG. 13B is another isometric i view of the drill guide and drills of FIG. 13A from a different direction.
Figures 14A, 14B:
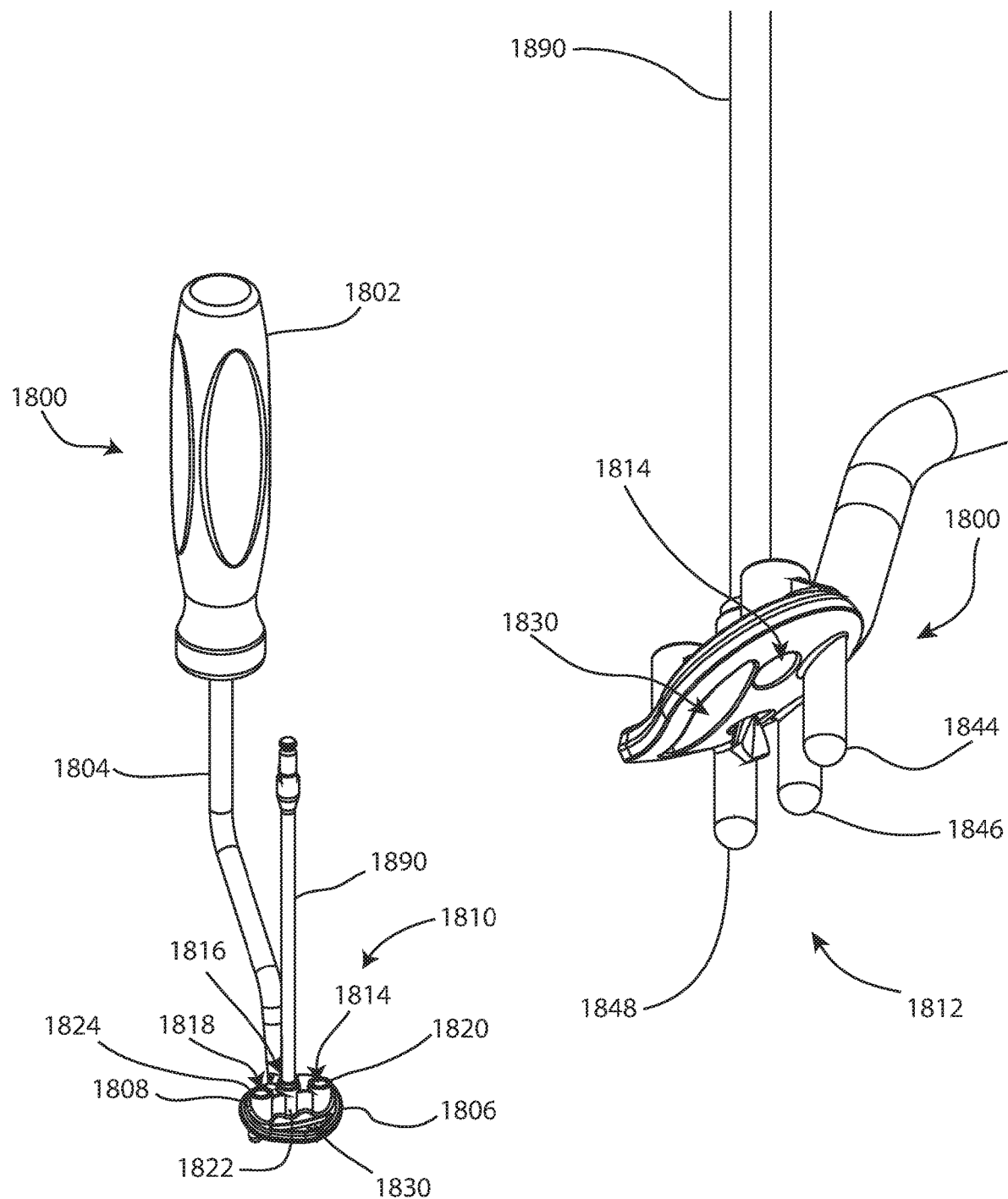
FIG. 14A is an isometric view of yet another drill guide with a drill.
FIG. 14B is another isometric view of the drill guide and drills of FIG. 14A from a different direction.
Figure 15A:
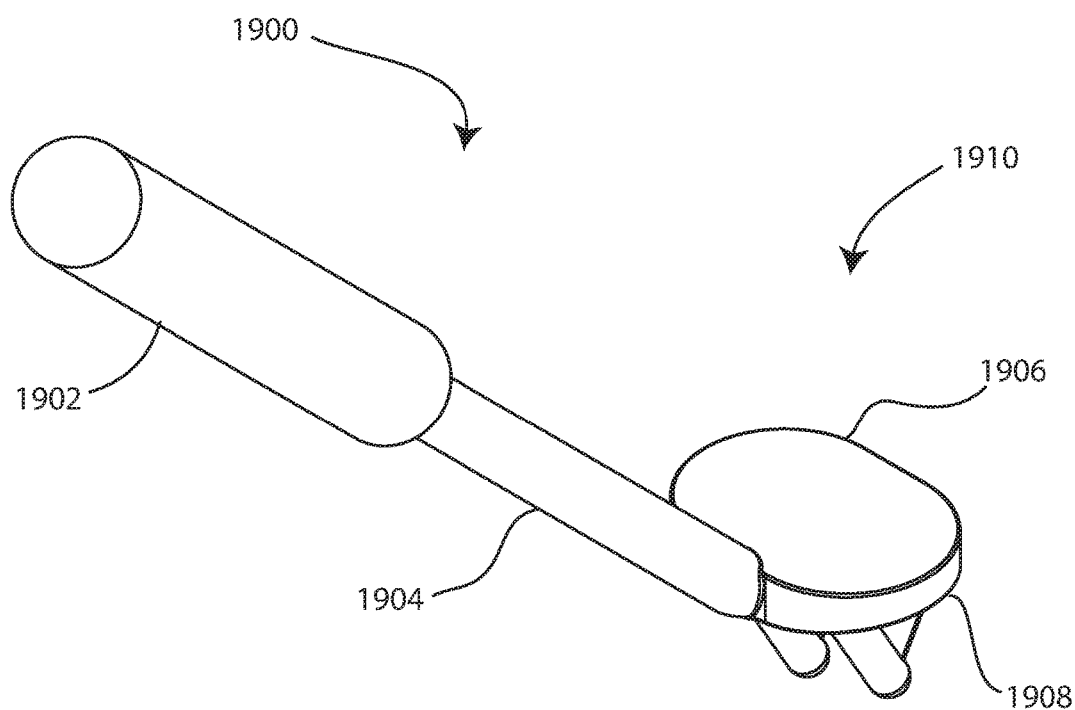
FIG. 15A is an isometric view of a punch.
Figure 15B:
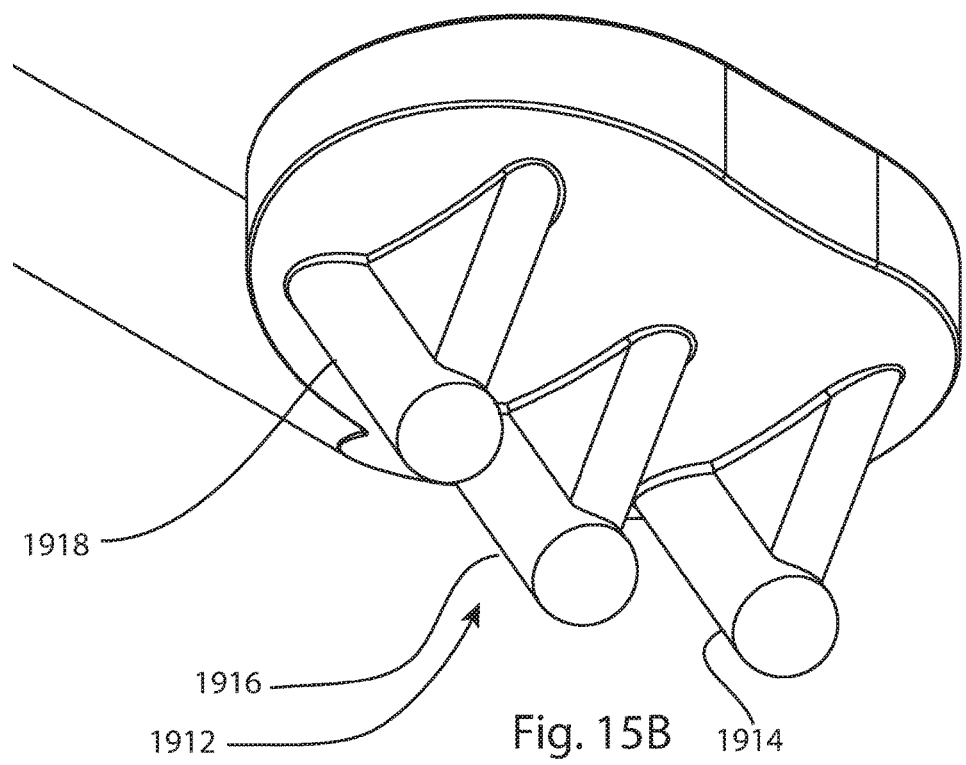
FIG. 15B is another isometric view of the punch of FIG. 15A from a different direction.
Figures 17A, 17B:
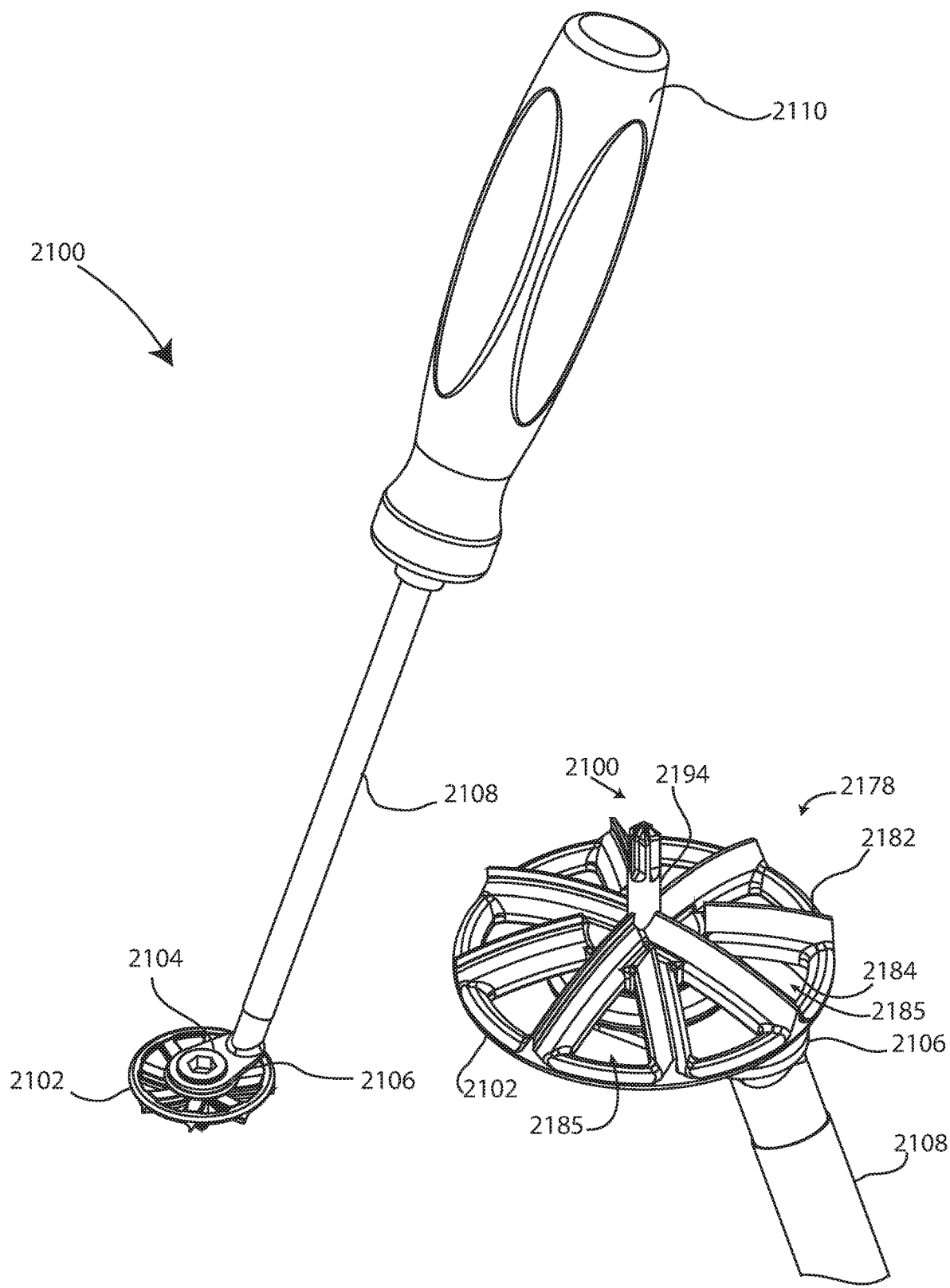
FIG. 17A is an isometric view of an offset reamer.
FIG. 17B is an isometric view of a portion of the offset reamer of FIG. 17A from a second viewpoint.
Figures 18A, 18B:
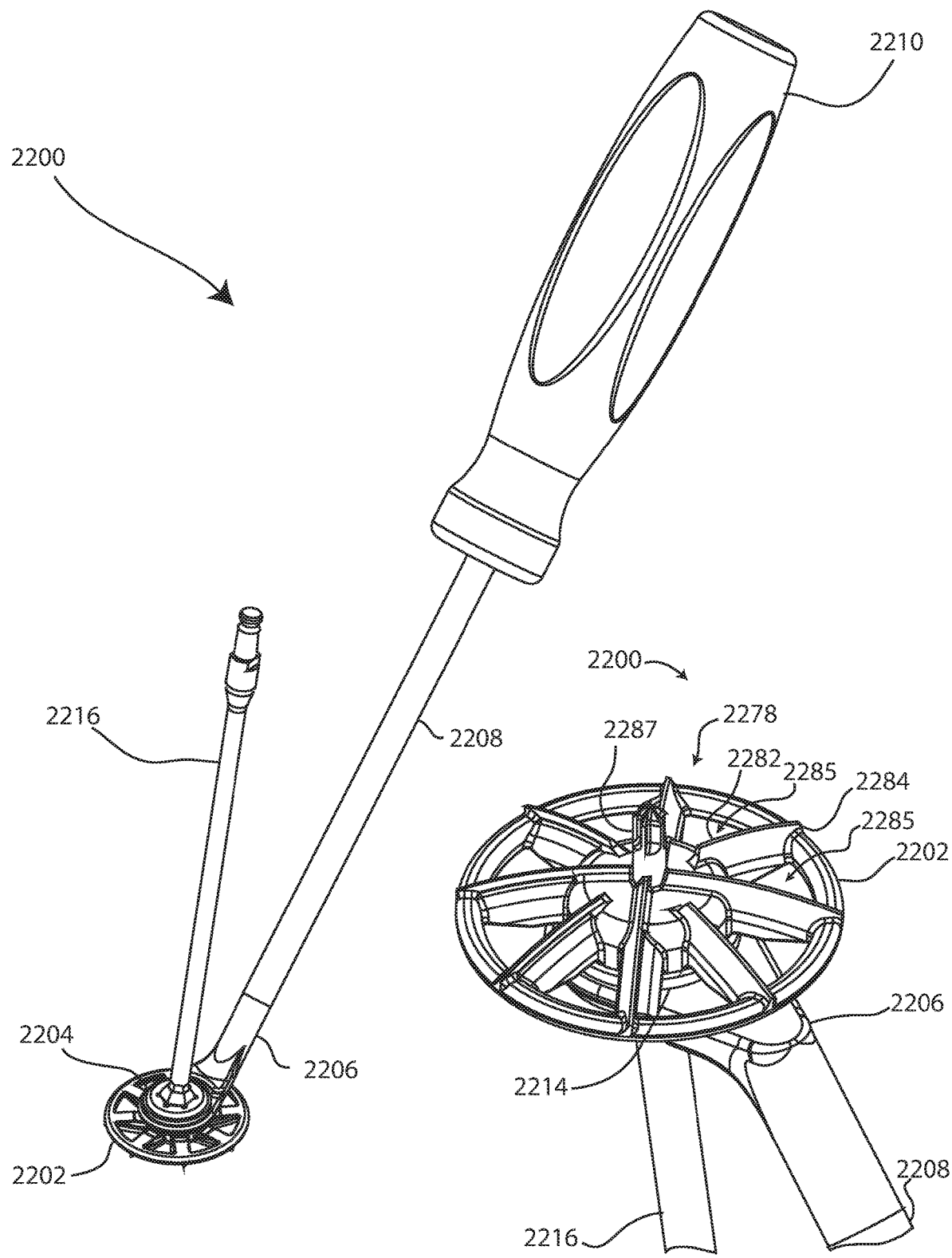
FIG. 18A is an isometric view of another offset reamer.
FIG. 18B is an isometric view of a portion of the offset reamer of FIG. 18A from a second viewpoint.
Figure 19:
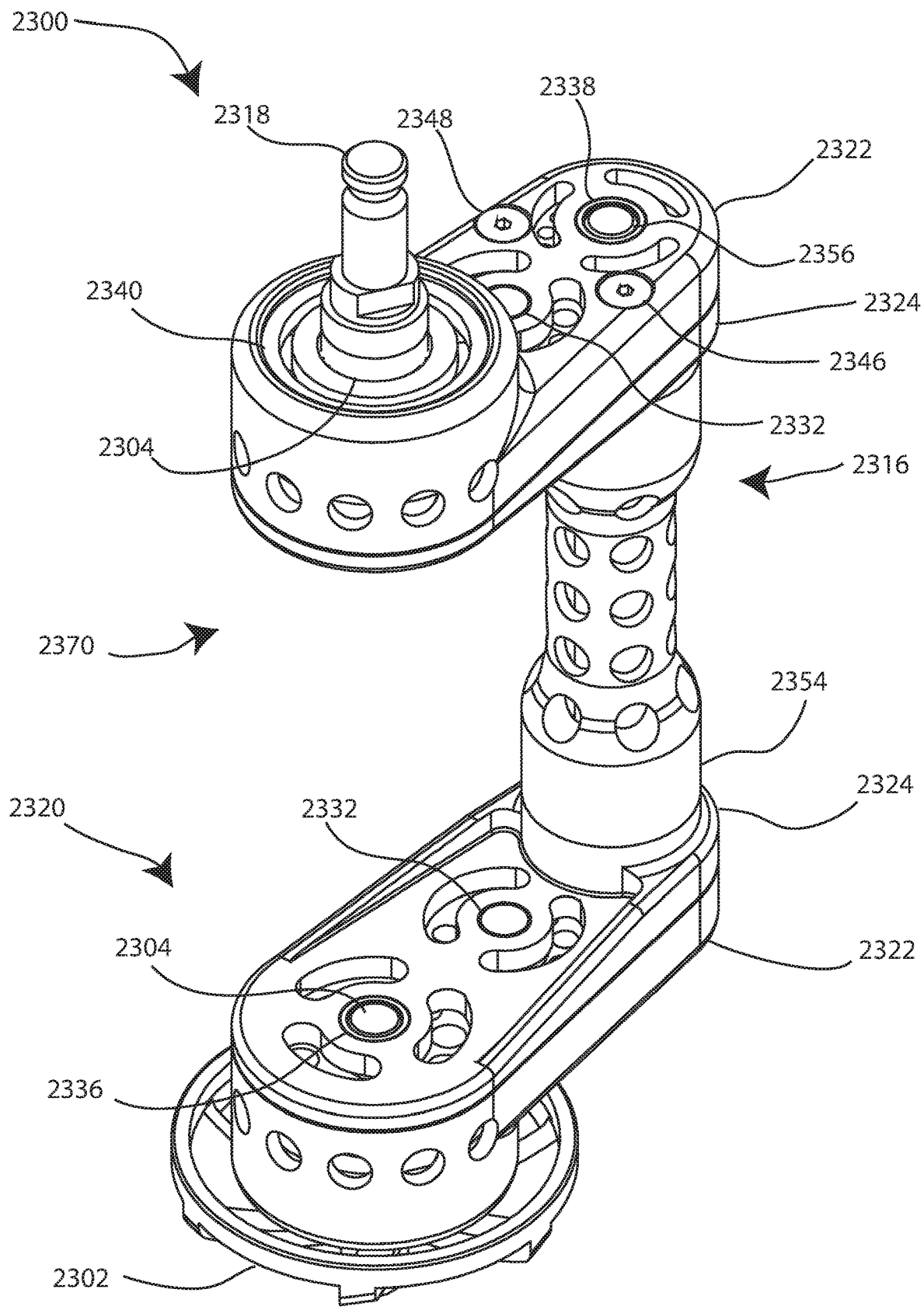
FIG. 19 is an isometric view of yet another offset reamer.
Figure 20:
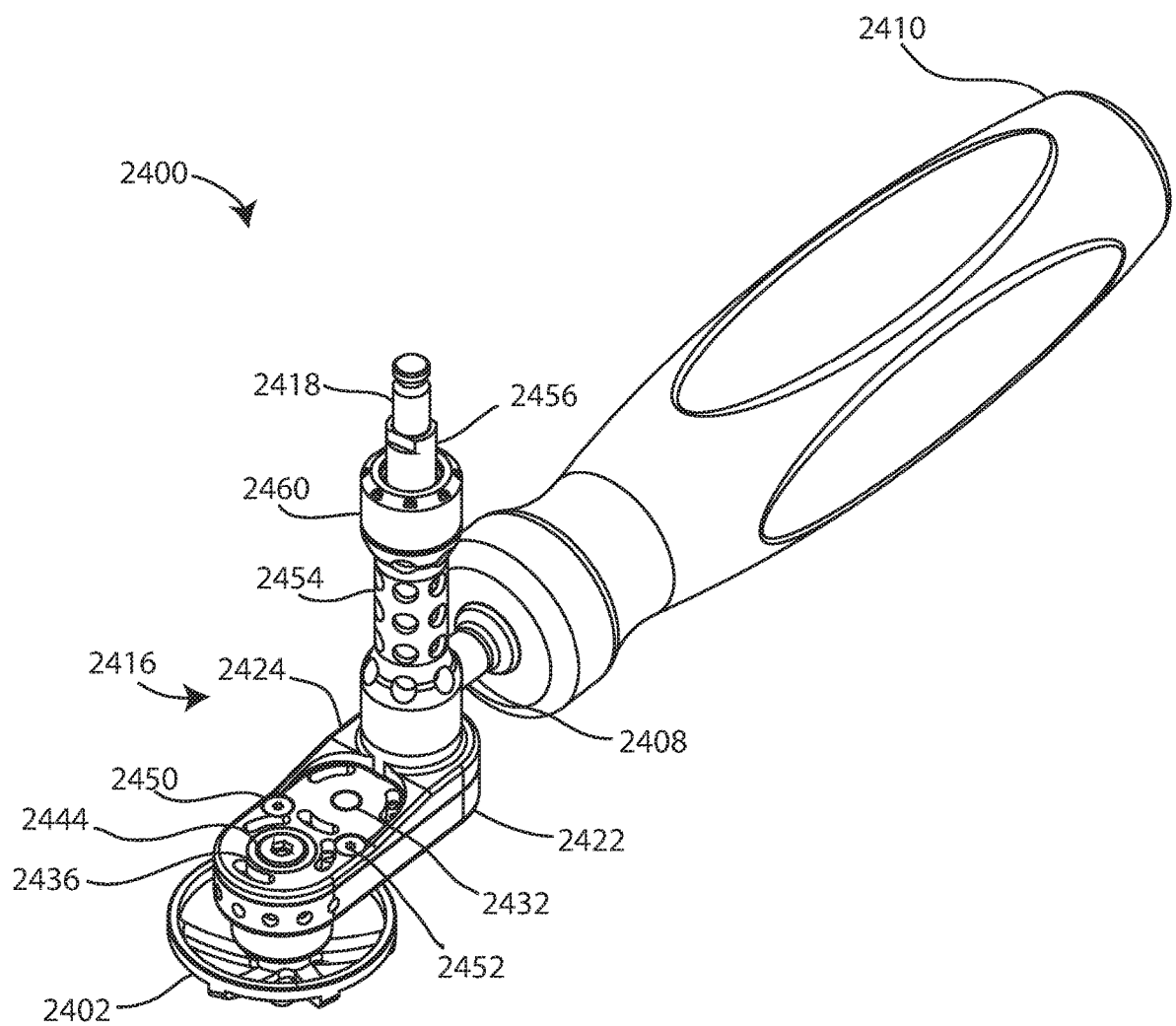
FIG. 20 is an isometric view of yet another offset reamer.
Figure 21:
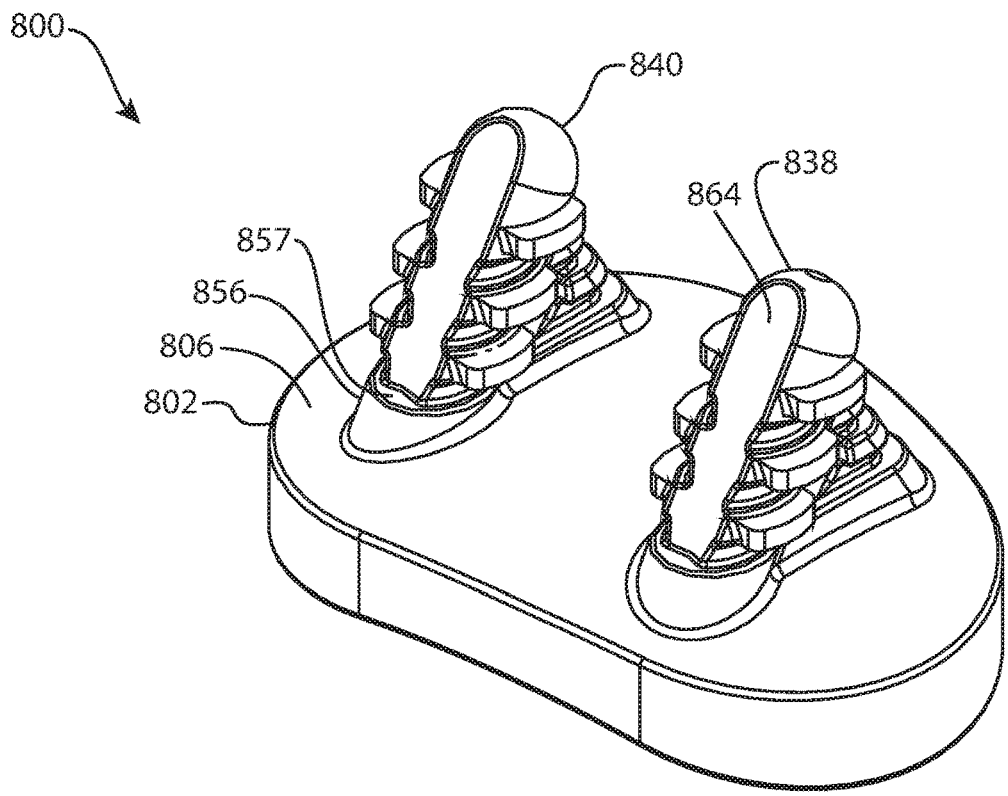
FIG. 21 is an isometric view of a left glenoid component.
Figure 22:
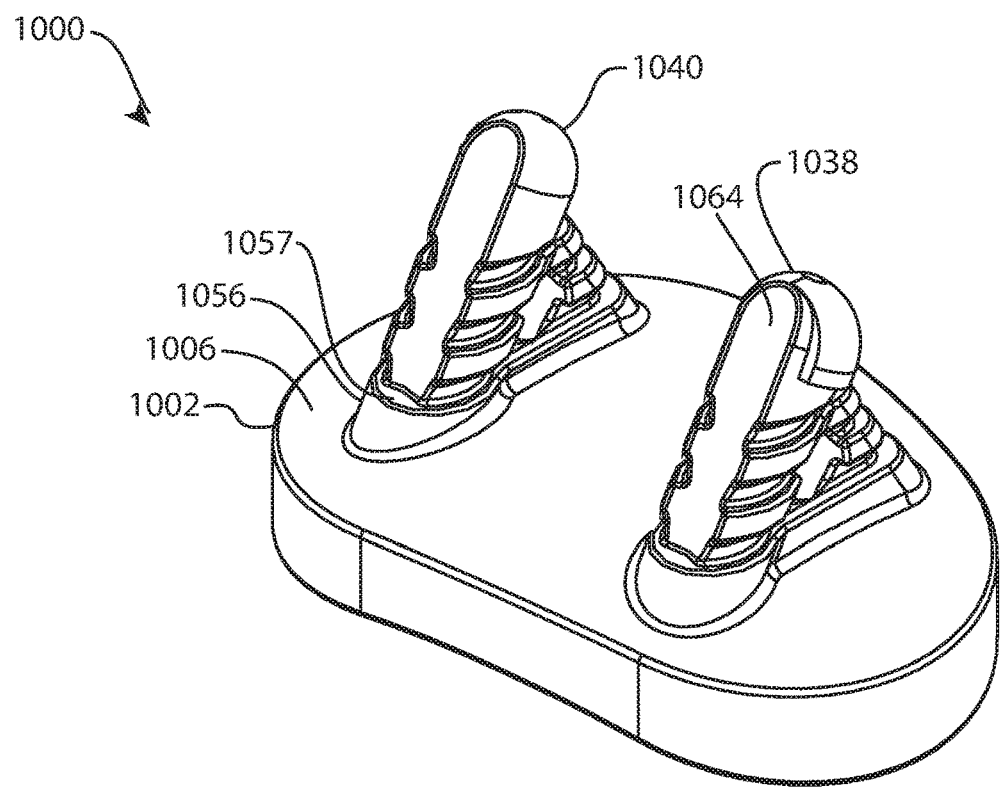
FIG. 22 is an isometric view of another left glenoid component.
Figure 23:
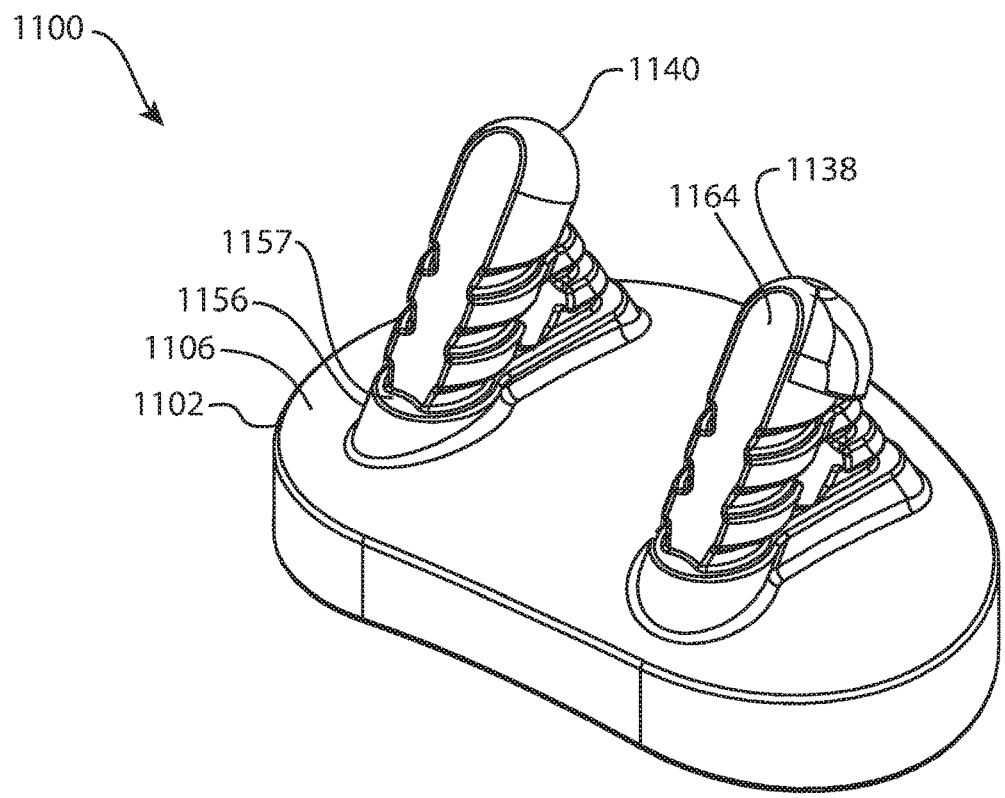
FIG. 23 is an isometric view of yet another left glenoid component.
Figure 24:
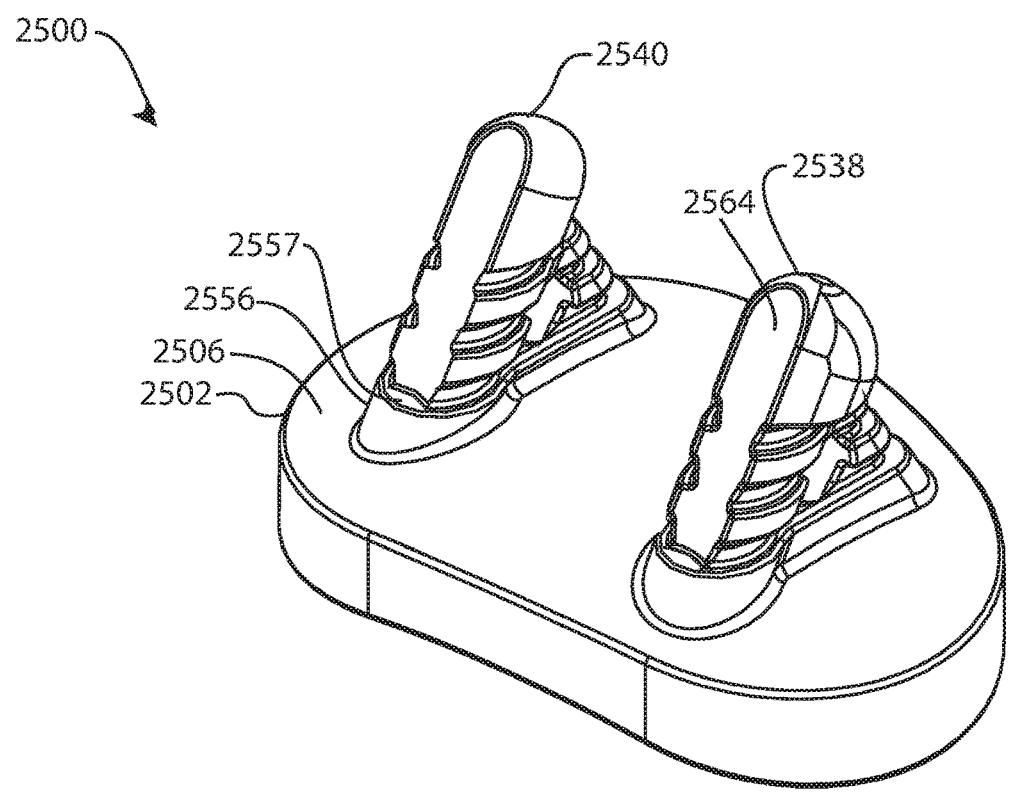
FIG. 24 is an isometric view of yet another left glenoid component.
Figure 25:
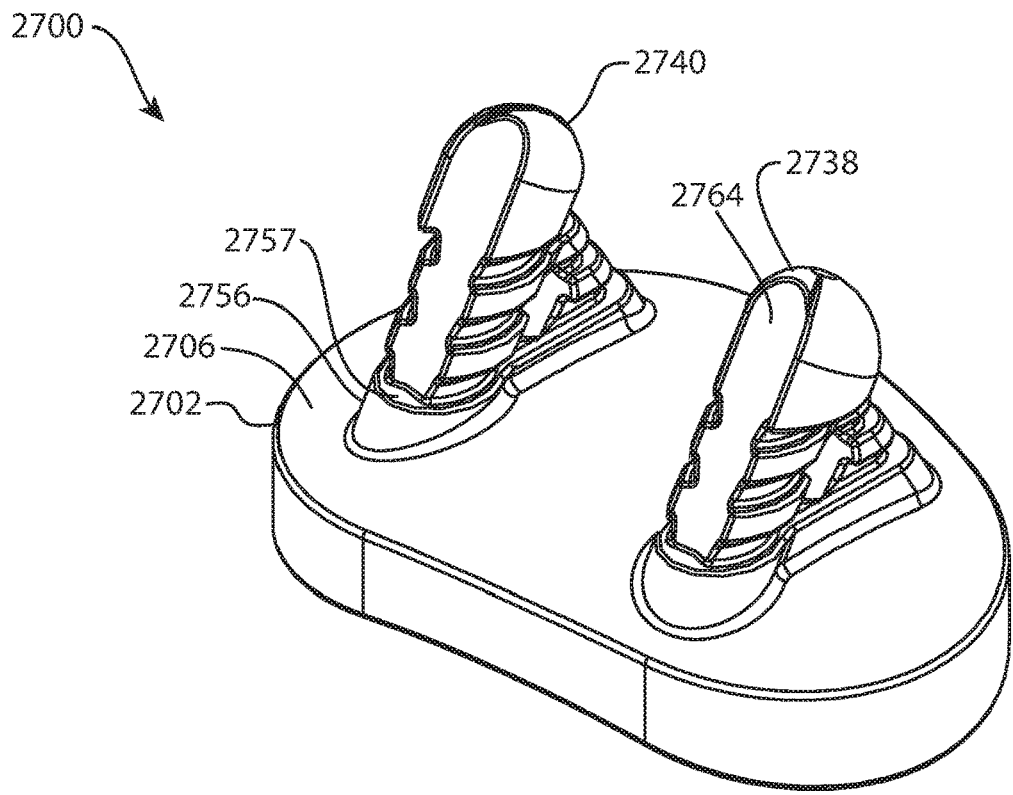
FIG. 25 is an isometric view of yet another left glenoid component.

The illustrated drill guide 4000 may be included in a system with the implants and/or instruments disclosed in U.S. patent application Ser. Nos. 14/042,258 and 15/587,895, including glenoid components 100, 200, 300, 400, 500, 600, 700 (FIGS. 1A-7B herein); sizing template 1200 (FIGS. 8A-8B herein); reamer 1300 (FIGS. 9A-9B herein); drill guides 1400, 1500, 1600, 1700, 1800 (FIGS. 10A-14B herein); punch 1900 (FIGS. 15A-15B herein); and broach 2000 (FIGS. 16A-16C herein). Furthermore, at least the sizing template 1200 and/or any of the drill guides 1400, 1500, 1600, 1700, 1800 may be adapted according to the principles disclosed herein.

The illustrated drill guide 4000 may be included in a system with the implants and/or instruments disclosed in U.S. patent application Ser. No. 14/592,837, including glenoid component 700 (FIGS. 7A-7B herein), reamer 1300 (FIGS. 9A-9B herein), and offset reamers 2100, 2200, 2300, 2400 (FIGS. 17A-20 herein).

The illustrated drill guide 4000 may be included in a system with the implants and/or instruments disclosed in U.S. patent application Ser. No. 15/228,443, including glenoid components 800, 1000, 1100, 2500, 2700, 2800, 2900 (FIGS. 21-27 herein).

The illustrated drill guide 4000 may be included in a system with the implants and/or instruments disclosed in U.S. patent application Ser. No. 15/653,305, including glenoid components 800, 1000, 1100, 2500, 2700, 2800, 2900, 3000, 3100, 3200, 3300, 3400, 3500, 3600, 3700, 3800, 3900 (FIGS. 21-33F herein).

The drill guide 4000 disclosed herein includes a guide body, or working portion 4200, and a handle 4400 with a shaft 4300. The guide body 4200 includes one or more cylindrical holes 4224, 4226 which serve as the guide(s) for a drill which is actuated through the hole(s). The drill guide 4000 controls the direction and/or the depth to which the drill is advanced into a bone, which dictates the shape of the hole made by the drill in the bone. The handle 4400 is held by the operator, and is used to hold the guide body 4200 against the bone into which the operator is drilling. The handle 4400 is not rigidly fixed to the guide body 4200 as is typical, but instead is coupled to the guide body 4200 by an articulation or joint which allows movement between the two parts. With this design, the operator can apply pressure along the handle 4400 to firmly secure the guide body 4200 against the bone, but once the guide body 4200 is secured against the bone, small movements of the operator's hand and the handle 4400 will not alter the position of the guide body 4200. The articulation or joint permits the handle 4400 to move relative to the guide body 4200, thus the guide body 4200 may remain stationary against the bone while a drill is actuated through the hole(s). This ensures that the holes created by the drill guide 4000 will be accurately placed in the intended position and/or depth and/or trajectory. Without the articulation or joing, small movements of the handle of the drill guide 4000 may alter the trajectory of the drill guide, then the trajectory of the drilled hole, and thus the final resting position of the implant inserted into that hole. Malpositioning of the drill guide, specifically the working portion 4200, may directly correlate to malpositioning of the implant, which puts the implant at risk for loosening or other failure modes.

The articulation may be a hinge joint, a universal joint, a ball-and-socket joint, a polyaxial joint, a saddle joint, or any other joint. A polyaxial joint is a joint that provides for rotation about at least two axes, wherein the second axis intersects or is skew to the first axis. The articulation may be a flexible shaft that couples the working portion 4200 to the handle 4400 or shaft 4300. The articulation may be spring biased. The articulation may be a magnetic joint that includes a magnet acting on a ferrous material, or magnets acting on each other. The articulation may be fixed (so that the guide body 4200 is captive to the handle 4400 or shaft 4300 in use, albeit free to move relative to the handle 4400), or may be dissociated into separate parts (so that the guide body 4200 is removable and connectable to the handle 4400 or shaft 4300 in use). The articulation or joint may include a first joint portion or joint feature carried by the working portion 4200 and a second joint portion or joint feature carried by the handle 4400 or shaft 4300. Some joint designs may include more than just two joint portions or joint features.

In an embodiment, the body 4202 of the drill guide 4000 contains a projection, or spike 4244, on the bone facing side which fits into a corresponding hole on the bone, which serves to resist side-side movement. In another embodiment, the body of the drill guide 4000 contains an additional hole or cannulation on the bone facing side into which a pin or dowel, anchored in the bone, is placed, which also serves to resist side-side movement. These are examples of stabilizing features that stabilize the body 4202 relative to a bone.

Figure 34:
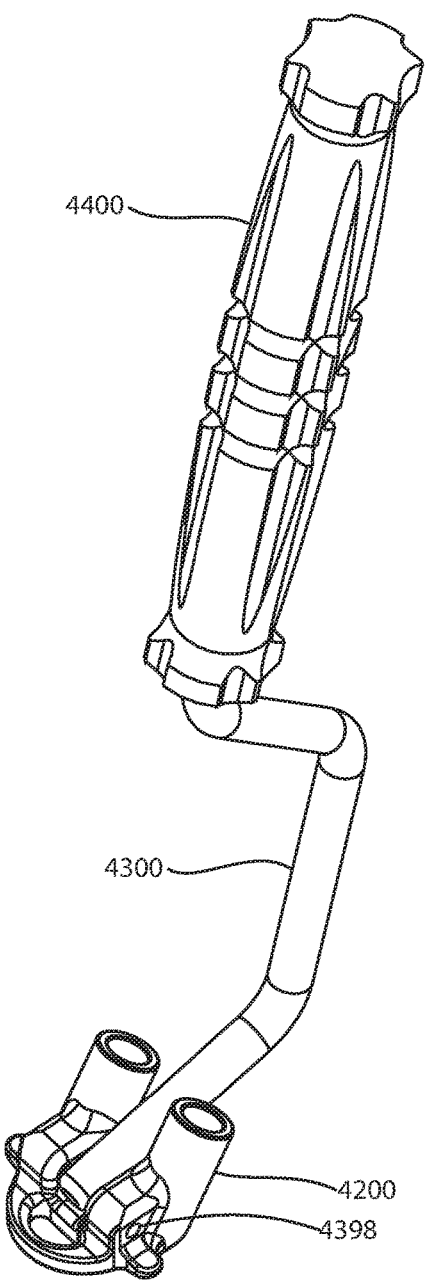
FIG. 34 is an isometric view of a drill guide.
Figure 35:
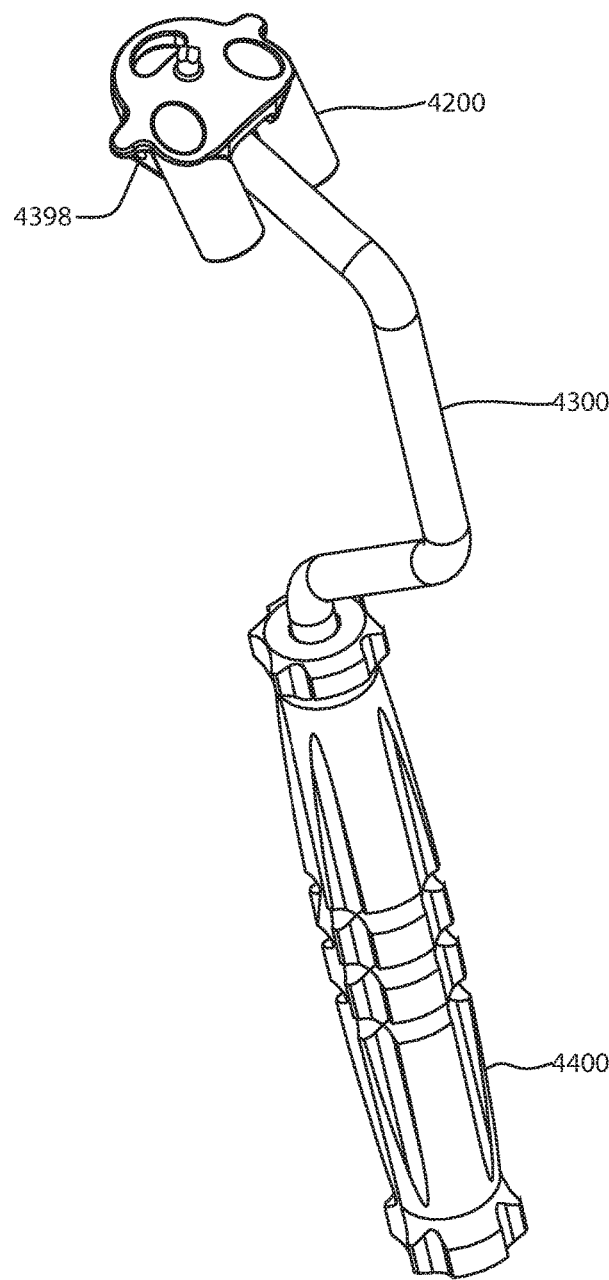
FIG. 35 is another isometric view of the drill guide of FIG. 34 from a different direction.
Figure 38:
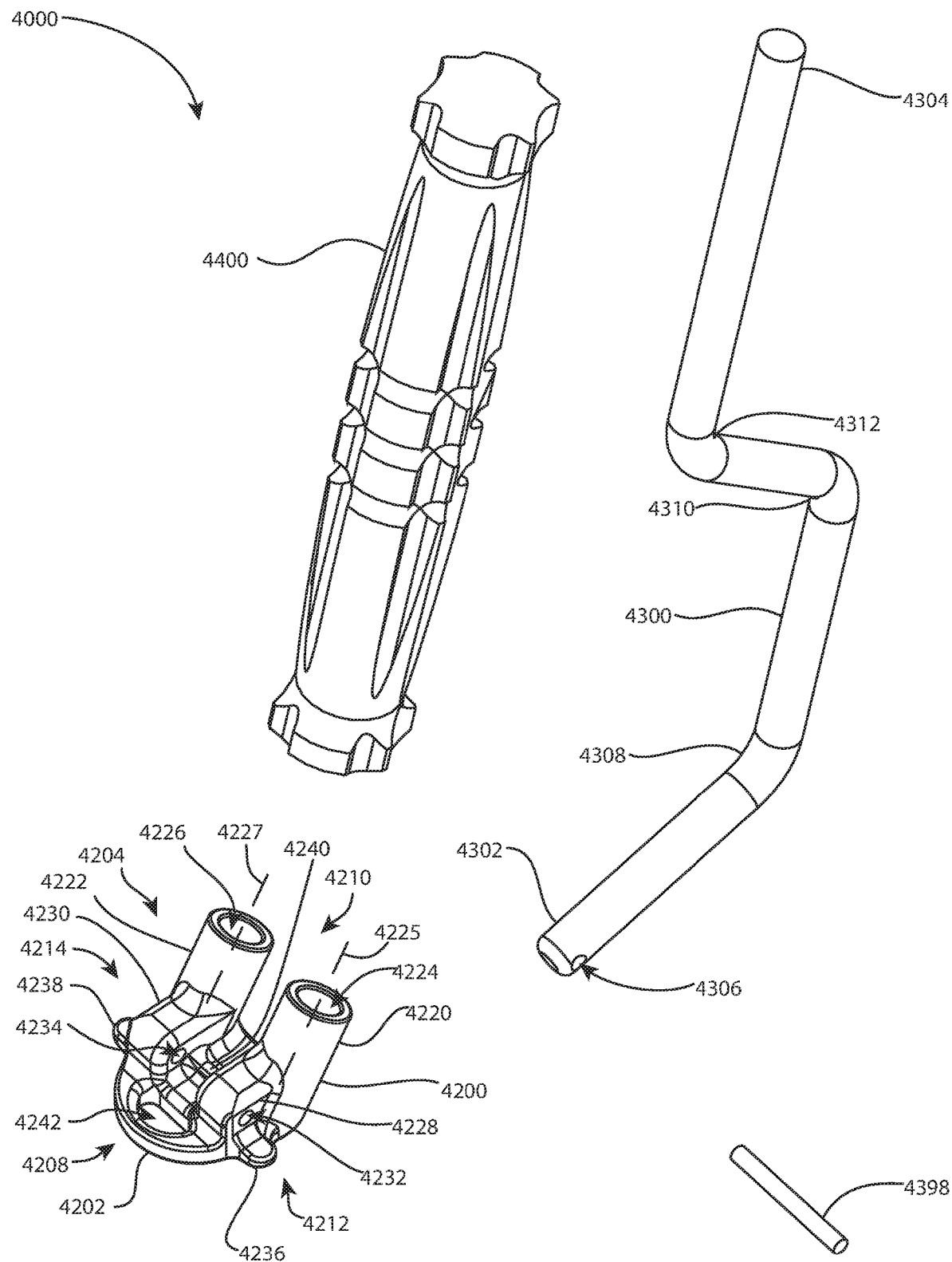
FIG. 38 is an isometric exploded view of the drill guide of FIG. 34.
Figure 39:
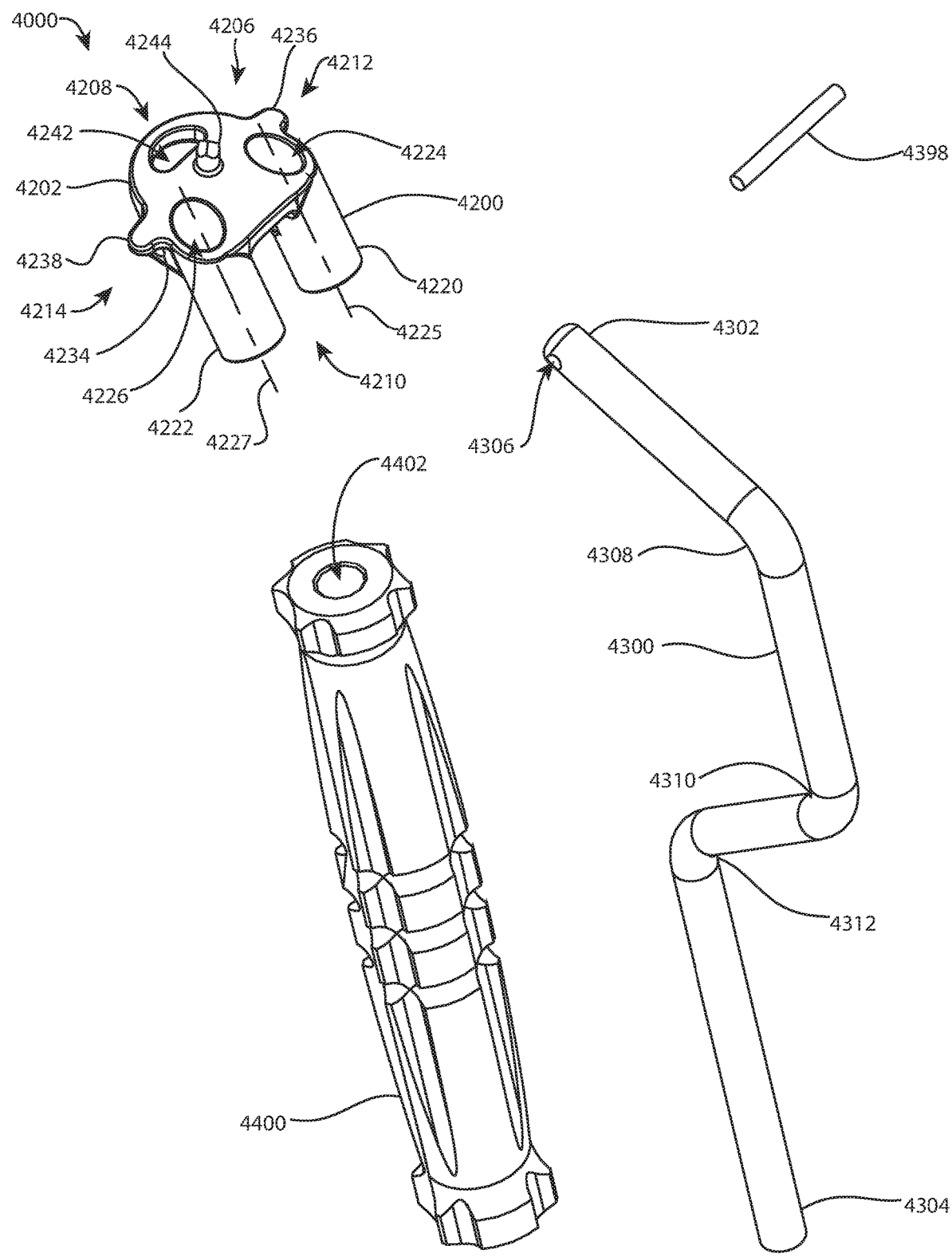
FIG. 39 is another isometric exploded view of the drill guide of FIG. 34 from a different direction.
Figure 40:
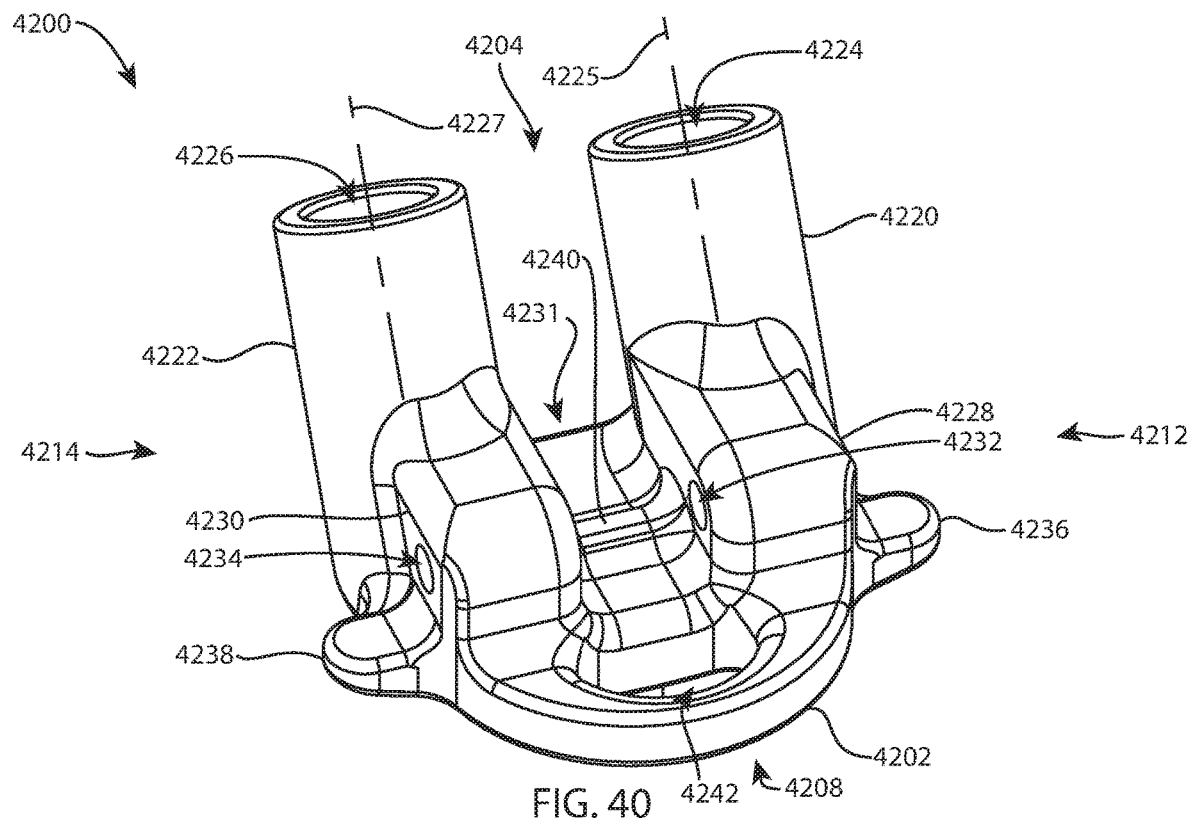
FIG. 40 is an isometric view of a working portion of the drill guide of FIG. 34.
Figure 41:
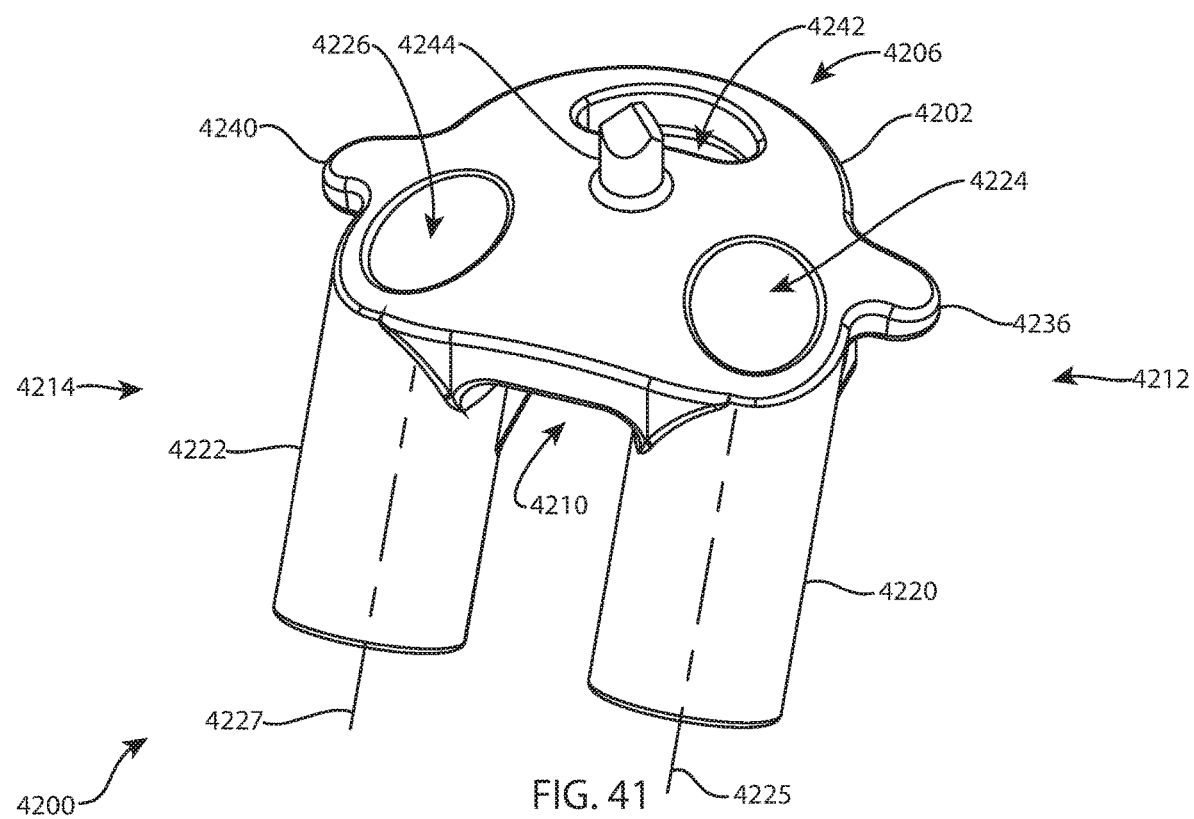
FIG. 41 is another isometric view of the working portion of FIG. 40 from a different direction.

Referring to FIG. 34, a drill guide 4000 may include a working portion 4200, a shaft 4300, a pin 4398, and a handle 4400. The working portion 4200 may be coupled to a first end (distal end) of the shaft 4300 by an articulation or a joint, and the handle 4400 may be coupled to a second end (proximal end) of the shaft 4300 opposite the working portion 4200. The shaft 4300 may be free to pivot relative to the working portion 4200 about the articulation or joint, which in this example is a hinge joint formed where the working portion 4200 is coupled to the shaft 4300 by the pin 4398. The handle 4400 may be rigidly fixed to the shaft 4300.

Referring to FIGS. 34-41, the working portion 4200 may be a bilaterally symmetric component with a plane of symmetry 4201 along section line 36B-36B of FIG. 36A.

The working portion 4200 may include a body 4202 with an obverse side 4204 and a reverse side 4206 opposite the obverse side. The obverse side 4204 may be referred to as a top side or proximal side, and the reverse side 4206 may be referred to as a bottom side or distal side. The body 4202 may also have a front side 4208, a back side 4210, a left side 4212, and a right side 4214. In use, the reverse side 4206 faces a bone surface such as a glenoid socket, while the obverse side 4204 faces away from the bone surface. The reverse side 4206 may be referred to as a bone facing side, and may make close contact with the bone surface. The reverse side 4206 is shown as a convex spherical surface. However, the reverse side 4206 need not be spherical, and may be flat (planar), concave, or otherwise shaped to complement a particular bone surface. The reverse side 4206 may be used against one or more natural bone surfaces, or against one or more bone resection surfaces, or a combination of natural and resected surfaces. The obverse side 4204 is shown as a planar surface (seen best in FIGS. 36B and 40). However, the obverse side 4204 may be convex, concave, or otherwise shaped as a matter of design choice.

In the example shown, the obverse side 4204 includes a left barrel 4220, a right barrel 4222, a left barrel hole 4224, a right barrel hole 4226, a left barrel hole axis 4225, a right barrel hole axis 4227, a left pin base 4228, a right pin base 4230, a left pin hole 4232, a right pin hole 4234, a left lateral tab 4236, and a right lateral tab 4238. The left and right barrels 4220, 4222 support the left and right barrel holes 4224, 4226, respectively. The left and right barrel holes 4224, 4226 extend completely through the working portion 4200 along the left and right barrel hole axes 4225, 4227, respectively. The left and right barrel hole axes 4225, 4227 are parallel to each other and to the plane of symmetry 4201 in this example, and they run in an oblique direction from obverse-back (top-back) to reverse-front (bottom-front). The left and right pin bases 4228, 4230 support the left and right pin holes 4232, 4234, respectively. The left and right pin holes 4232, 4234 are coaxial and may share the same diameter. Together, the left and right pin holes 4232, 4234 may be thought of as a single pin hole that extends completely through the working portion 4200 from left to right, perpendicular to the plane of symmetry 4201. The left and right pin holes 4232, 4234 may be referred to as a joint portion or joint feature of the working portion 4200; the joint portion or joint feature may also include the left and right pin bases 4228, 4230. The left and right lateral tabs 4236, 4238 project outwardly from the body 4202 and may be located below the left and right pin holes 4232, 4234 or elsewhere. The left and right lateral tabs 4236, 4238 are examples of anatomical reference features that may be included in the drill guide 4000, preferably in the working portion 4200. Along the plane of symmetry 4201, the obverse side 4204 includes a slot 4231, a ridge 4240 and an aperture 4242. The slot 4231 extends from front to back between the left and right pin bases 4228, 4230. The joint portion or joint feature may also include the slot 4231. The ridge 4240 runs from left to right between the left and right pin bases 4228, 4230. The aperture 4242 extends completely through the body 4202 from obverse to reverse near the front side 4208.

The reverse side 4206 includes a central spike 4244. The spike 4244 may include a trocar point as shown, a drill tip, or it may be blunt. The spike 4244 is one example of a stabilizing feature that stabilizes the working portion 4200 relative to a bone. The left and right barrel holes 4224, 4226 and the aperture 4242 extend through the reverse side 4206; the left and right lateral tabs 4236, 4238 extend to the reverse side 4206.

Other embodiments of the working portion may be designed differently from the working portion 4200. For example, other embodiments may be asymmetric instead of bilaterally symmetric, or they may have another type of symmetry besides bilateral symmetry. Other embodiments may lack clearly defined front, back, left, and right sides, although these basic directional terms may still be employed with these embodiments even if some or all of these four sides are indistinguishable from each other. Other embodiments may have only one barrel, barrel hole, barrel hole axis, pin base, pin hole, and/or tab; yet other embodiments may have more than two barrels, barrel holes, barrel hole axes, pin bases, pin holes, and/or tabs. A single barrel hole and its corresponding barrel hole axis may be inclined at an oblique angle relative to the reverse side as shown, or they may be at any other angle relative to the reverse side, including perpendicular or parallel, according to the design constraints for a particular surgical site. Multiple barrel holes and their corresponding barrel hole axes may all be parallel as shown, or they may be arranged at any other relative angle, including oblique, acute, obtuse, or perpendicular, according to the design constraints for a particular surgical site. Multiple barrel holes and their corresponding barrel hole axes may be located as desired on the working portion, for example in a linear array, a circular array, or in another arrangement, according to the need for bone holes for a particular application of the technology. The pin base(s) and pin hole(s) may be replaced with another feature or features to provide any of the types of joints discussed previously. The tab(s) may be oriented according to the anatomical landmarks for a particular surgical site, and may be replaced with grooves or other indicia as a matter of design choice.

Referring to FIGS. 34-39, the shaft 4300 is an elongated part that extends between a first end 4302 (distal end) and an opposite second end 4304 (proximal end). The first end 4302 may be referred to as a working end and the second end 4304 may be referred to as a handle end. The first end 4302 includes a transverse pin hole 4306 which extends completely through the shaft 4300. The hole 4306 may be referred to as a joint portion or joint feature of the shaft 4300. The shaft 4300 may be straight, or it may include one or more bends. Three bends 4308, 4310, 4312 are shown. Of the three, the bend 4308 is closest to the first end 4302, the bend 4312 is closest to the second end 4304, and the bend 4310 is between the bends 4308, 4312. Referring to FIG. 37, the three bends 4308, 4310, 4312 cooperate to bend a first portion of the shaft 4300 between the bend 4312 and the first end 4302 laterally relative to a second portion of the shaft 4300 between the bend 4312 and the second end 4304. Thus the first portion of the shaft 4300 between the bend 4312 and the first end 4302 is laterally offset relative to the second portion of the shaft 4300. However, in this example, the first end 4302 remains substantially in line with the second portion of the shaft and the second end 4304. The shaft may be designed differently according to the design constraints for a particular surgical site.

The working portion 4200 may be assembled to the first end 4302 of the shaft 4300 by inserting the first end 4302 between the left and right pin bases 4228, 4230 so that the pin hole 4306 is aligned with the left and right pin holes 4232, 4234 and the first portion of the shaft 4300 is oriented as shown in FIG. 37, offset from the back side 4210 of the body 4202. The pin 4398 may then be inserted into the holes 4306, 4232, 4234. The pin 4398 may have a press fit in one of the three holes and a loose fit in the remaining two holes. The shaft 4300 is free to pivot relative to the working portion 4200 about the pin 4398, as indicated by the double ended range of motion arrow 4396 in FIG. 36B. In the example shown, the shaft 4300 has a range of motion 4396 about the pin 4398 between a first position shown in FIG. 36B, in which the shaft 4300 touches the ridge 4240, and a second position, in which the shaft 4300 touches the obverse front portion of the body 4202. The ridge 4240 and the obverse front portion of the body 4202 act as range of motion stops at each end of the range of motion 4396.

The shaft 4300 may be assembled to the handle 4400 by pressing the second end 4304 of the shaft 4300 into a hole 4402 in one end (distal end) of the handle. Alternatively, the second end 4304 and the hole 4402 may be provided with complementary external and internal threads, respectively. Other means for rigid, secure assembly are contemplated. The shaft 4300 and handle 4400 may be detachably coupled together. When the shaft 4300 and the handle 4400 are coupled together, whether permanently or detachably, they may be referred to collectively as a handle portion of the drill guide 4000.

The drill guide 4000 may include an optional biasing element or biasing mechanism (not shown) to bias the shaft 4300 to a particular neutral position relative to the working portion 4200. For example, with reference to FIG. 36B, the shaft 4300 may be biased to the first position. The biasing element or mechanism may be a spring, a group of springs, a magnet, a cam, a drag pin, or the like. This arrangement may be advantageous, particularly when the working portion 4200 is being inserted into a surgical site for use, because it may stabilize the shaft 4300 relative to the working portion 4200 so that the user can control the position of the working portion 4200 against a bone surface. After the working portion 4200 is inserted and positioned against the bone surface, the user may then temporarily overcome the bias to move the shaft 4300 relative to the working portion 4200. The bias may preferably be light enough (low force) so that small unintentional movements of the shaft 4300 and/or handle 4400 are isolated by the joint between the shaft 4300 and the working portion 4200.

The drill guide 4000 may include an optional user-selectable control or lockout (not shown) that stabilizes or immobilizes the shaft 4300 relative to the working portion 4200 when the control is in a first setting and permits free movement of the shaft 4300 relative to the working portion 4200 when the control is in a second setting. For example, a cable or mechanical linkage may be strung through a cannulation in the shaft 4300 to couple a handle-mounted control to a mechanism near the joint.

Figure 26:
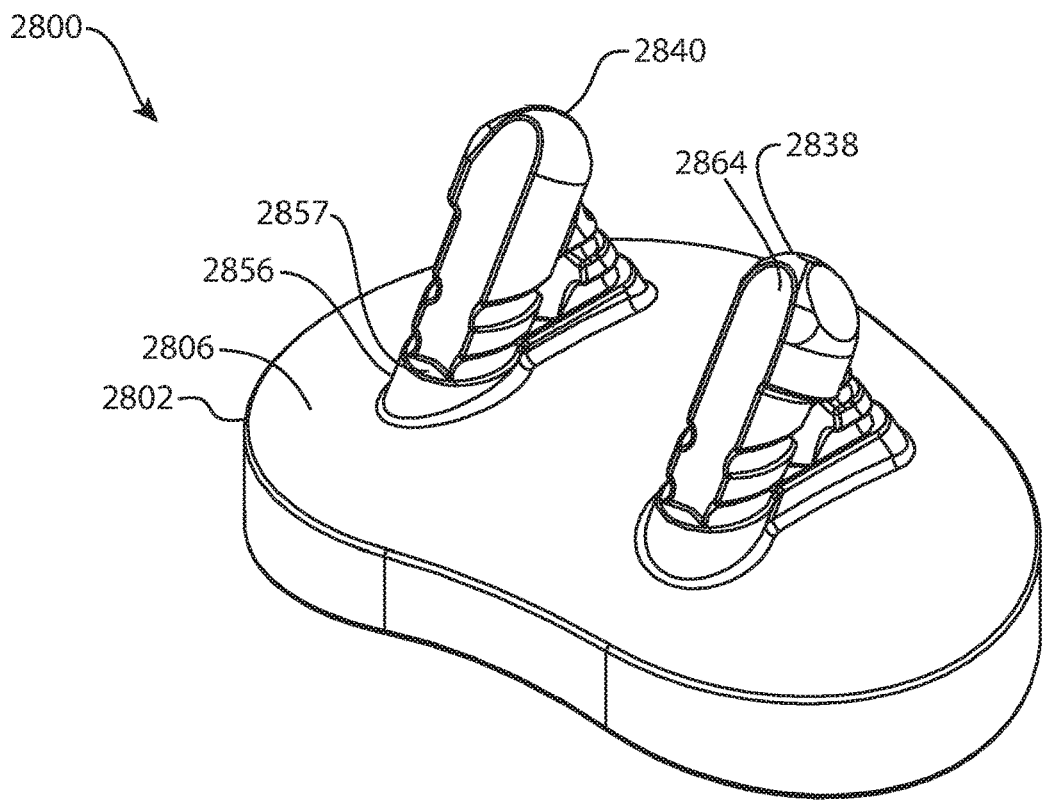
FIG. 26 is an isometric view of yet another left glenoid component.
Figure 27:
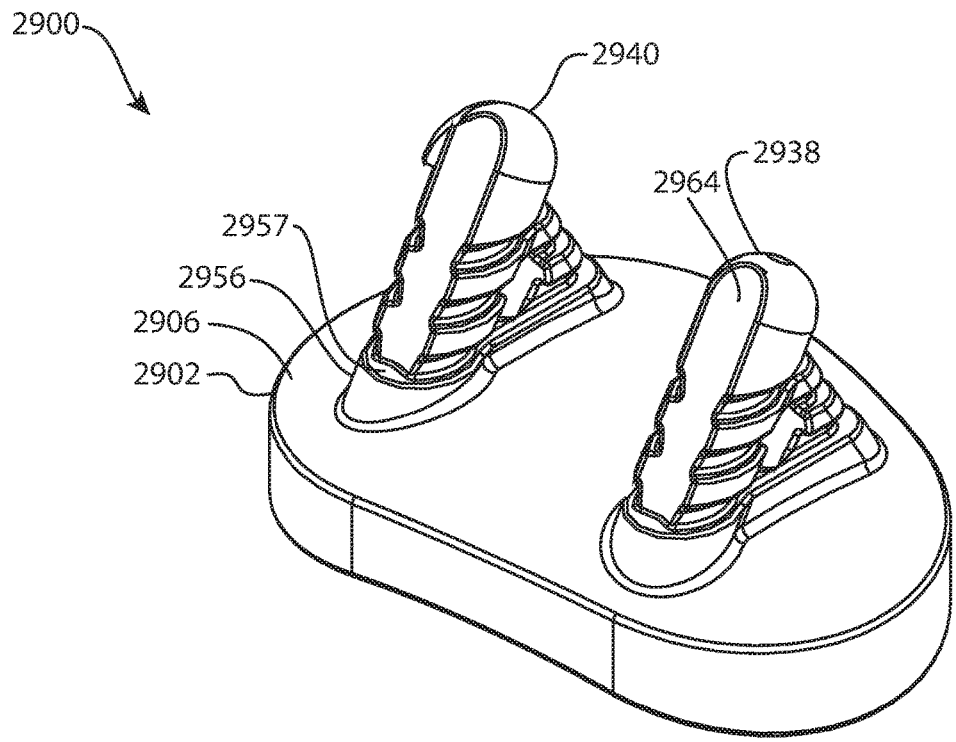
FIG. 27 is an isometric view of yet another left glenoid component.
Figures 28A, 28B:
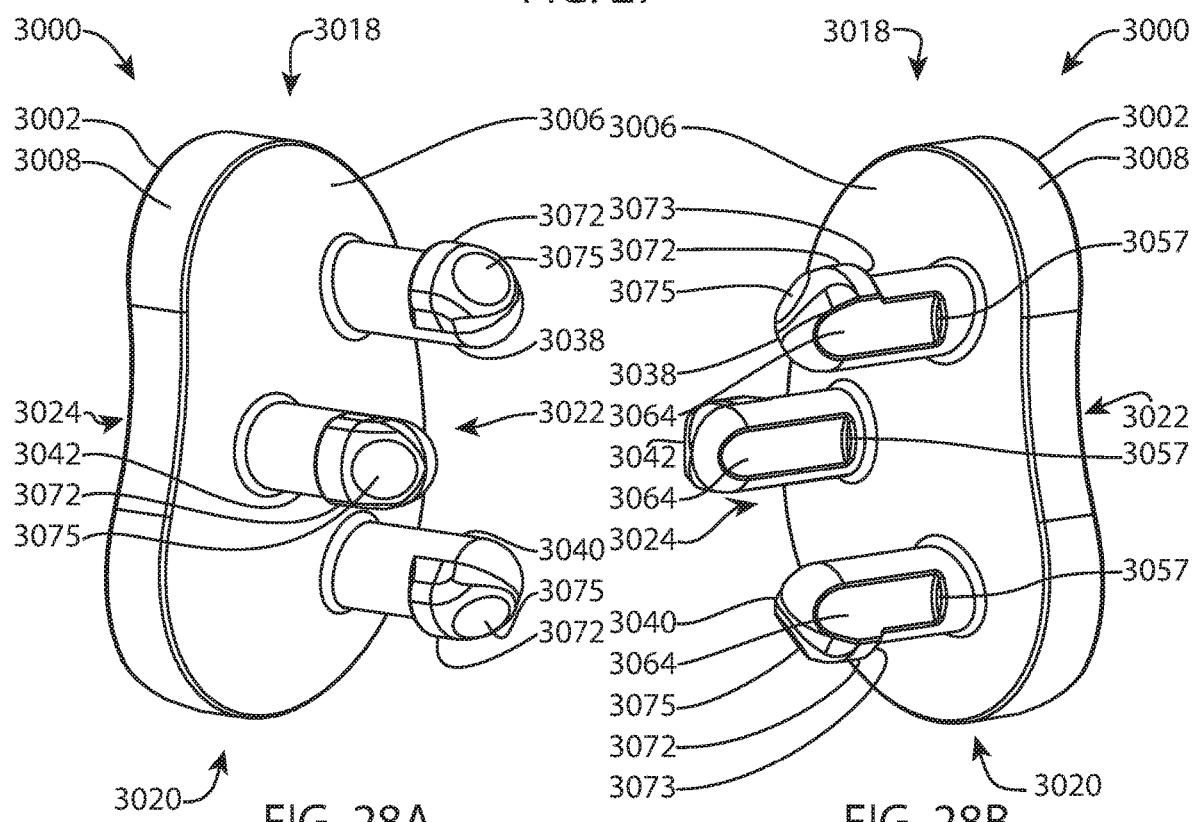
FIG. 28A is a medial-superior-posterior view of yet another glenoid component.
FIG. 28B is a medial-superior-anterior view of the glenoid component of FIG. 28A.
Figure 42:
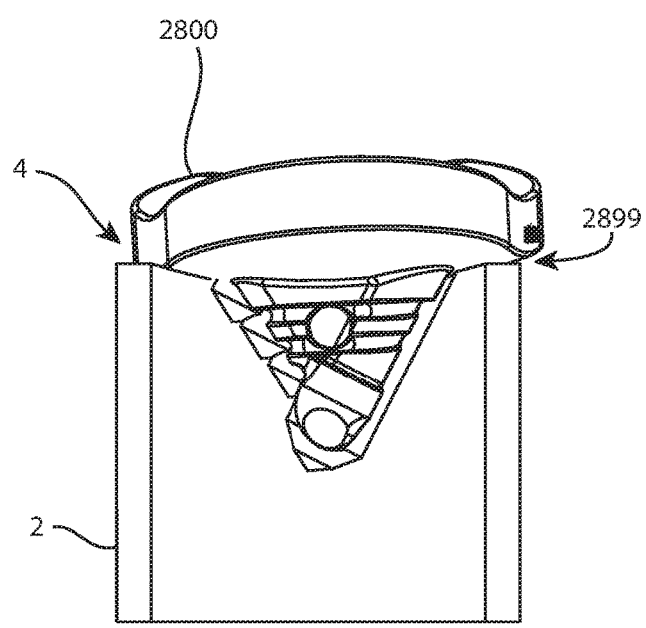
FIG. 42 is a superior view of the glenoid component of FIG. 26 implanted in a prepared bone socket in a glenoid fossa of a scapula.
Figure 43:
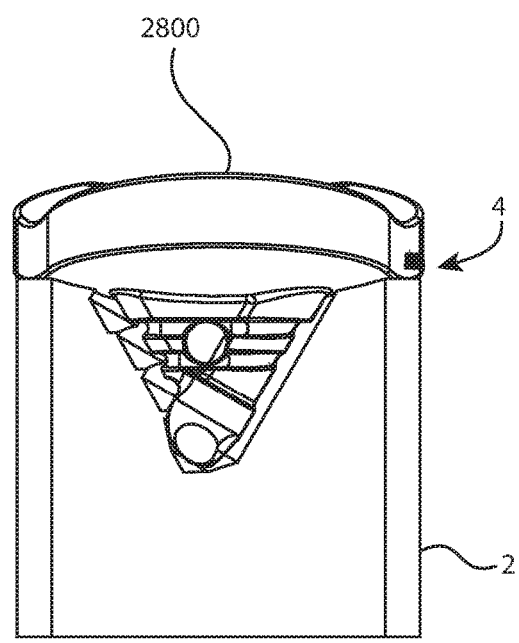
FIG. 43 is a superior view of the glenoid component of FIG. 26 implanted in another prepared bone socket in a glenoid fossa of a scapula.

Referring to FIGS. 42 and 43, the glenoid component 2800 of FIG. 26 is shown inserted into prepared bone sockets in the glenoid fossa 4 of a scapula 2. The scapula 2 is shown in a simplified representation. The glenoid component 2800 could be replaced by any of the other glenoid components disclosed herein, along with a complementary bone socket. FIG. 42 illustrates a malpositioned bone socket that is two or three degrees away from proper alignment. Note that the glenoid component 2800 appears to be shifted to the right (anterior) relative to the scapula 2. However, the glenoid component 2800 may actually be tilted, due to its fit in the bone socket, so that the right (anterior) side of the glenoid lifts off of the glenoid and a gap 2899 is present. The right (anterior) side of the glenoid component 2800 may therefore be unsupported, which puts the glenoid component at increased risk of loosening over time, and may cause premature failure of the fixation element due to increased stress. This effect may be exacerbated in a glenoid component designed with a flat bone facing surface and/or a straight fixation peg. Glenoid component failure may cause the patient to undergo revision surgery. Glenoid component loosening is the most common cause of revision shoulder arthroplasty surgery. FIG. 43 illustrates a properly positioned bone socket and glenoid component 2800. This glenoid component is solidly seated on the glenoid and properly supported for long term success.

A method of using the drill guide 4000 may include some or all of the following steps in any order: inserting the spike 4244 into a complementary hole in a bone surface; positioning the reverse side 4206 against the bone surface; aligning the left and/or right lateral tab 4236, 4238 with one or more anatomical directions or anatomical landmarks; pivoting the shaft 4300 with attached handle 4400 about the pin 4398 relative to the working portion 4200 within the range of motion 4396; and drilling a bone hole through one or both of the left and right barrel holes 4224, 4226.

These steps may be preceded by one or more steps of resecting bone to form one or more resected bone surfaces.

The step of pivoting the shaft 4300 about the pin 4398 relative to the working portion 4200 is advantageous for at least the following reasons.

Firstly, unintentional movements of the user's hand, the handle 4400, and/or the shaft 4300 are not transferred to the working portion 4200 as they would be in a conventional, completely rigid drill guide. More specifically, in the example shown, unintentional movements which cause rotation about the pin 4398 are not transferred. In other examples, the hinge joint formed by the pin 4398 in the holes 4306, 4232, 4234 may be replaced by a ball and socket joint (or other polyaxial joint), in which case unintentional movements which cause rotation about the center point of the ball and socket joint would not be transferred.

Secondly, the user may intentionally pivot the shaft 4300 about the pin 4398 relative to the working portion 4200 so that the shaft 4300 may be used as a retractor or pry bar to lever surrounding anatomical structures out of the way, without disturbing the position of the working portion 4200. In the context of glenoid arthroplasty, for example, the humeral head may be in the way when attempting to drill into the glenoid socket. The shaft 4300 may be pivoted toward the second position to push the humeral head away from its anatomical position relative to the glenoid socket.

Thirdly, the shaft 4300 may be positioned relative to the working portion 4200 to avoid contacting surrounding anatomical structures.

In the context of glenoid arthroplasty, the step of aligning the left and/or right lateral tab 4236, 4238 with an anatomical direction or bony landmark may mean aligning the left and right lateral tabs 4236, 4238 with the superior-inferior direction.

The method may also include the step of inserting a glenoid component into a prepared glenoid fossa of a scapula. This step may include the step of applying bone cement to the prepared glenoid fossa before inserting the glenoid component.

The method may also include steps of using other instruments in conjunction with the drill guide 4000.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A drill guide comprising:
a working portion comprising a bone-facing side, an obverse side opposite the bone-facing side comprising a right pin hole and a left pin hole, and a barrel hole that extends through at least a portion of the working portion and comprises a barrel hole axis, wherein the barrel hole receives a drill with clearance; and
a shaft comprising a transverse pin hole, the shaft coupled to the working portion by a hinge pin inserted through the right pin hole, the transverse pin hole, and the left pin hole, wherein the right pin hole, the transverse pin hole, and the left pin hole are coaxial with each other along a central longitudinal axis of the hinge pin, wherein the shaft is movable within a plane of symmetry relative to the working portion about the central longitudinal axis of the hinge pin, such that the shaft pivots about the central longitudinal axis of the hinge pin within the plane of symmetry while the shaft is coupled to the working portion by the hinge pin, wherein the central longitudinal axis of the hinge pin is perpendicular to the plane of symmetry and the barrel hole axis is parallel to the plane of symmetry, and wherein the shaft is coupled to the working portion before the barrel hole receives the drill.

2. The drill guide of claim 1, wherein a joint of the drill guide comprises:
the right pin hole of the obverse side of the working portion;
the left pin hole of the obverse side of the working portion;
the transverse pin hole of the shaft; and
the hinge pin inserted through the right pin hole, the transverse pin hole, and the left pin hole.

3. The drill guide of claim 2, wherein the joint is a hinge joint between the shaft and the working portion.

4. The drill guide of claim 3, wherein the shaft is movable relative to the working portion about the hinge joint while the drill is actuated in the barrel hole.

5. The drill guide of claim 3, wherein the shaft is movable relative to the working portion about the hinge joint within a range of motion, wherein the obverse side of the working portion comprises at least one range of motion stop associated with the hinge joint.

6. The drill guide of claim 5, comprising a biasing element that biases the shaft to contact the at least one range of motion stop.

7. The drill guide of claim 1, wherein the working portion is captive to the shaft.

8. The drill guide of claim 1, comprising a locking mechanism comprising a first setting and a second setting;
wherein when the locking mechanism is in the first setting, the shaft is immobilized relative to the working portion;
wherein when the locking mechanism is in the second setting, the shaft is freely movable relative to the working portion.

9. The drill guide of claim 1, wherein:
the shaft is pivotable about the central longitudinal axis of the hinge pin within the plane of symmetry between a first position next to a first end of the working portion and a second position next to a second end of the working portion opposite the first end, such that the shaft pivots about the central longitudinal axis of the hinge pin within the plane of symmetry as the shaft is moved between the first and second positions.

10. The drill guide of claim 1, wherein:
the central longitudinal axis of the hinge pin is perpendicular to the barrel hole axis.

11. The drill guide of claim 1, wherein:
a distal end of the shaft is coupled to the working portion by the hinge pin inserted through the transverse pin hole of the shaft, and
the distal end of the shaft pivots about the central longitudinal axis of the hinge pin within the plane of symmetry between a first inclined position next to a first end of the working portion and a second inclined position next to a second end of the working portion opposite the first end of the working portion, such that the distal end of the shaft pivots about the central longitudinal axis of the hinge pin within the plane of symmetry as the distal end of the shaft is moved from the first inclined position away from the first end of the working portion, and toward the second end of the working portion to the second inclined position.

12. A drill guide comprising:
a working portion comprising a pin hole and a barrel hole having a barrel hole axis, wherein the barrel hole receives a drill with clearance; and
a shaft comprising a transverse pin hole, the shaft coupled to the working portion by a hinge pin inserted through the pin hole and the transverse pin hole, wherein the pin hole and the transverse pin hole are coaxial with each other along a central longitudinal axis of the hinge pin, wherein the shaft is movable within a plane of symmetry relative to the working portion about the central longitudinal axis of the hinge pin, such that the shaft pivots about the central longitudinal axis of the hinge pin within the plane of symmetry while the shaft is coupled to the working portion by the hinge pin, wherein the central longitudinal axis of the hinge pin is perpendicular to the plane of symmetry and the barrel hole axis is parallel to the plane of symmetry, and wherein the shaft is disconnected from the drill.

13. The drill guide of claim 12, wherein the shaft is movable relative to the working portion about the central longitudinal axis of the hinge pin within the plane of symmetry while the drill is actuated in the barrel hole.

14. The drill guide of claim 12, wherein:
the shaft is pivotable about the central longitudinal axis of the hinge pin within the plane of symmetry between a first position next to a first end of the working portion and a second position next to a second end of the working portion opposite the first end, such that the shaft pivots about the central longitudinal axis of the hinge pin within the plane of symmetry as the shaft is moved between the first and second positions.

15. The drill guide of claim 12, wherein:
the central longitudinal axis of the hinge pin is perpendicular to the barrel hole axis.

16. The drill guide of claim 12, wherein:
the shaft is pivotable about the central longitudinal axis of the hinge pin within the plane of symmetry between a first inclined position next to a first end of the working portion and a second inclined position next to a second end of the working portion opposite the first end of the working portion, such that the shaft pivots about the central longitudinal axis of the hinge pin within the plane of symmetry as the shaft is moved
from the first inclined position away from the first end of the working portion, and
toward the second end of the working portion to the second inclined position.

* * * * *